US012790409B2

(12) United States Patent
Watters et al.

(10) Patent No.: US 12,790,409 B2
(45) Date of Patent: Nov. 10, 2026

(54) HISTAMINE BINDING POLYPEPTIDES AND USES THEREOF

(71) Applicant: PRESIDENT AND FELLOWS OF HARVARD COLLEGE, Cambridge, MA (US)

(72) Inventors: Alexander Watters, Cambridge, MA (US); Pawan Jolly, Boston, MA (US); Donald E. Ingber, Boston, MA (US); Thomas Cunningham, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 835 days.

(21) Appl. No.: 18/014,863

(22) PCT Filed: Jul. 6, 2021

(86) PCT No.: PCT/US2021/040424
§ 371 (c)(1),
(2) Date: Jan. 6, 2023

(87) PCT Pub. No.: WO2022/010830
PCT Pub. Date: Jan. 13, 2022

(65) Prior Publication Data
US 2023/0287142 A1 Sep. 14, 2023

Related U.S. Application Data

(60) Provisional application No. 63/048,352, filed on Jul. 6, 2020.

(51) Int. Cl.
*C07K 16/44* (2006.01)
*C12N 15/63* (2006.01)
*G01N 33/68* (2006.01)

(52) U.S. Cl.
CPC .............. *C07K 16/44* (2013.01); *C12N 15/63* (2013.01); *G01N 33/6812* (2013.01); *C07K 2317/565* (2013.01); *C07K 2317/622* (2013.01)

(58) Field of Classification Search
CPC .................. A61K 9/0019; C07K 16/44; C07K 2317/565; C07K 2317/622; C12N 15/63; G01N 33/6812
(Continued)

(56) References Cited

U.S. PATENT DOCUMENTS 5,112,738 A * 5/1992 Buckler ............... C07D 233/64 435/7.93
2020/0181249 A1 6/2020 Curtis et al.
2020/0190171 A1 6/2020 Schneyer

FOREIGN PATENT DOCUMENTS

CN 110028579 A * 7/2019
WO 2018141863 A1 8/2018

OTHER PUBLICATIONS

Machine Translation of CN 110028579 A, published Jul. 19, 2019.*
International Search Report and Written Opinion mailed Dec. 30, 2021 in PCT/US21/40424.

* cited by examiner

*Primary Examiner* — Christopher L Chin
*Assistant Examiner* — Ellis Follett Lusi
(74) *Attorney, Agent, or Firm* — Nixon Peabody LLP; David S. Resnick; Ravinderjit S. Braich

(57) ABSTRACT

Described herein are polypeptides, compositions, kits, and analyte detection systems for the detection of the presence or absence of small molecules (e.g. histamine and/or histidine) in a test sample.

14 Claims, 5 Drawing Sheets

Specification includes a Sequence Listing.

(58) Field of Classification Search
USPC ................ 435/7.1; 530/387.1, 388.1, 388.15
See application file for complete search history.

Biotin-PEG-histamine

Biotin-PEG-mono-histidine

Biotin-PEG-dual-histidine

Biotin-PEG-Phenyl-histamine

Chemical Formula: $C_{42}H_{66}N_{10}O_{10}S$
Exact Mass: 902.468
Molecular Weight: 903.110

HISTAMINE BINDING POLYPEPTIDES AND USES THEREOF

CROSS-REFERENCE TO RELATED APPLICATIONS

This Application is a 35 U.S.C. § 371 National Phase Entry Application of International Application No. PCT/US2021/040424, filed Jul. 6, 2021, which claims benefit under 35 U.S.C. § 119(e) of the U.S. Provisional Application No. 63/048,352 filed Jul. 6, 2020, the contents of both of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 22, 2021, is named 002806-097650WOPT_SL.txt and is 39,457 bytes in size

TECHNICAL FIELD

The technology described herein relates to polypeptides, compositions, kits, and analyte detection systems for the detection of the presence or absence of small molecules (e.g. histamine and/or histidine) in a test sample.

BACKGROUND

Small-molecule detection is important for many applications including clinical diagnostics, drug discovery, and measurements of environmental samples and agricultural products. Current techniques for small-molecule detection suffer from various limitations including low analytical sensitivity and complex sample processing.

Furthermore, very small molecules, such as histamine (11.14 g/mol) which consists of an imidazole ring and a short carbon chain terminated with a primary amine, pose even more of a challenge due in part to their limited functionalities.

The importance of histamine in various physiological functions and its involvement in allergenic responses make this small molecule one of the most studied biogenic amines. Histamine is not only the major mediator of the acute inflammatory and immediate hypersensitivity responses, but has also been demonstrated to affect chronic inflammation and regulate several essential events in the immune response. It can influence numerous functions of the cells involved in the regulation of immune response and hematopoiesis including macrophages, dendritic cells, T lymphocytes, B lymphocytes and endothelial cells.

Dysregulation or imbalances of the histamine system can be a leading contributor to a variety of disease states and symptoms, many of which can be debilitating or life-disruptive. For example, abnormally high histamine levels can lead to excessive allergies (or hyperactive responses to allergens), hyperactivity, compulsive or obsessive behavior, vertigo, inner ear pressure, depression, anxiety, panic attacks, migraine headaches, heightened emotional sensitivity and/or suicidal tendencies. Reduced histamine levels can lead to depressed metabolism and/or weight gain, paranoia, grandiosity, hallucinations (e.g., classic schizophrenic symptoms), tinnitus, hirsutism, visual and auditory abnormalities, anxiety and food sensitivities.

Thus, analytical methods for the detection of histamine with great specificity and sensitivity have great potential value for medical diagnostics (e.g., for allergy and anaphylaxis), early detection of diseases, and food safety applications. Even though a variety of chromatography-based methods have been described for its analytical determination, the disadvantages they present in terms of cost, analysis time, and low portability limit their suitability for in situ routine testing. Current, antibody-based diagnostical methods utilize antibodies against histamine raised by conjugating histamine to a large immunogenic protein carrier, such as bovine serum albumin (BSA) or ovalbumin (OVA) via its primary amine group. Consequently, only the imidazole will be exposed to lymphocytes, which commonly results in generation of antibodies that recognize protein-bound histamine with only limited affinity and sensitivity for free histamine. These antibodies typically perform poorly in the development of immunoassays.

Thus, there remains a need in the art for compositions and methods for the detection of free histamine. The present disclosure addresses some of these needs.

SUMMARY

Embodiments of various aspects described herein, include novel polypeptides, compositions comprising the same, kits, and analyte detection systems for detecting the presence or absence of a small molecule (e.g. histamine and/or histidine) in a test sample. Some embodiments provide methods of treatments for diseases or conditions resulting from dysregulations and/or imbalances of the histamine and/or histidine system.

In one aspect of any of the embodiments, provided herein is a polypeptide comprising: (a) a variable heavy chain (VH) domain comprising (i) a complementarity determining region 1 (VH CDR1) comprising an amino acid sequence having at least 85% identity to an amino acid sequence selected from the group consisting of: AVALGGNMN (SEQ ID NO: 1) and YSFTGYNMN (SEQ ID NO: 2), (ii) a complementarity determining region 2 (VH CDR2) comprising an amino acid sequence having at least 85% identity to an amino acid sequence selected from the group consisting of: WIGNIAVAIGLTRY (SEQ ID NO: 3) and WIGNINPYYGSTRY (SEQ ID NO: 4), and (iii) a complementarity determining region 3 (VH CDR3) comprising an amino acid sequence having at least 85% identity to the amino acid sequence selected from the group of RDDDYGEIDYFDY (SEQ ID NO: 5) and RAGVKGNILAAGN (SEQ ID NO: 83); and (b) a variable light chain (VL) domain comprising: (i) a complementarity determining region 1 (VL CDR1) comprising an amino acid sequence having at least 85% identity to an amino acid sequence selected from the group consisting of: QSIVHSNGNTYLE (SEQ ID NO: 6), QSLVHSGGNTYLE (SEQ ID NO: 7), QSIVHSSGNTYLE (SEQ ID NO: 8), QSLVHSSGNTYLE (SEQ ID NO: 9), QSIVHSGGNTYLE (SEQ ID NO: 10), QTIVHSNGNTYLE (SEQ ID NO: 11), QSIVHSDGNTYLE (SEQ ID NO: 12), QSIVSSSGNTYLE (SEQ ID NO: 13), QSIVYSDGNTYLE (SEQ ID NO: 14), QTIVHSSGNTYLE (SEQ ID NO: 15), QSIVHRDGNTYLE (SEQ ID NO: 16), QSLVHSDGNTYLE (SEQ ID NO: 17), QTIVHSNGNTYLE (SEQ ID NO: 18), GVAGANAGAGALA (SEQ ID NO: 19), and QSIVYSSGNTYLE (SEQ ID NO: 20); (ii) a complementarity determining region 1 (VL CDR2) comprising an amino acid sequence having at least 85% identity to an amino acid sequence selected from the group consisting of: LLIYAVKATGA (SEQ ID NO: 21), LLIYKVSNRFS (SEQ ID NO: 22); and (iii) a complementarity determining region 1 (VL CDR3) comprising an amino acid sequence selected from the group consisting of: SQATHVPY (SEQ ID NO: 23), AGAVAVAA (SEQ ID NO: 24) and FQASHVPY (SEQ ID NO: 25).

In some embodiments of any of the aspects, provided herein is a composition comprising a polypeptide described herein.

In some embodiments of any of the aspects, provided herein is a cell comprising a polypeptide described herein.

In some embodiments of any of the aspects, provided herein is a kit comprising a polypeptide described herein.

In some embodiment of any of the aspects, provided herein is an analyte detection system comprising a polypeptide described herein.

In another aspect of any of the embodiments, described herein is the use of a polypeptide described herein for detecting histamine and/or histidine.

In some embodiments of any of the aspects, provided herein is a polynucleotide comprising a nucleotide sequence encoding a polypeptide described herein.

In some embodiments of any of the aspects, provided herein is a cell comprising a polynucleotide described herein.

In some embodiments of any of the aspects, provided herein is a kit comprising a polynucleotide described herein.

DETAILED DESCRIPTION

Figure 1B:
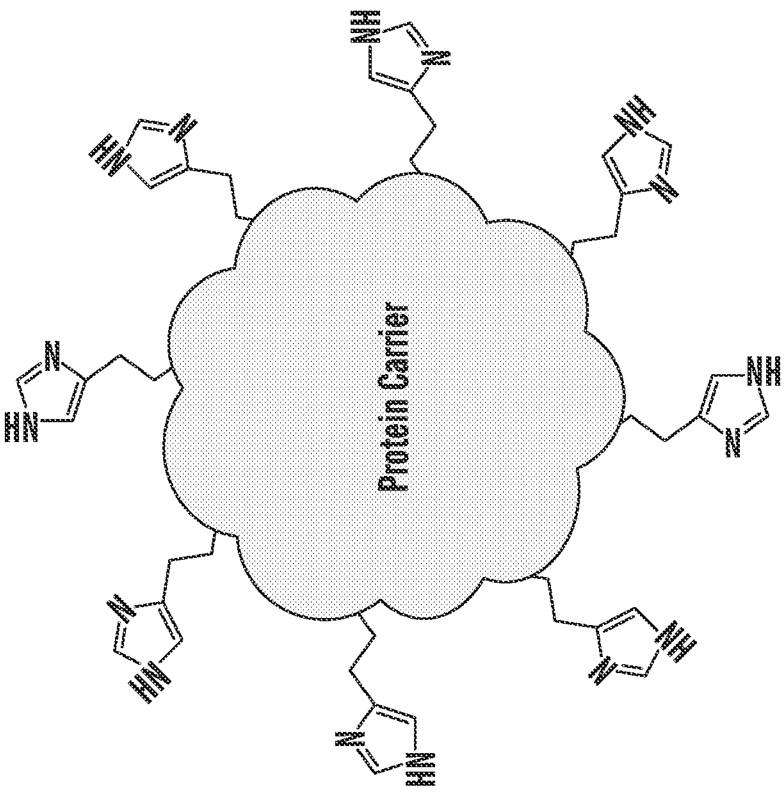
FIG. 1B depicts a typical Histamine-Protein carrier conjugate.

Provided herein are novel polypeptides, compositions comprising the same, kits, and analyte detection systems for detecting the presence or absence of a small molecule (e.g. histamine and/or histidine) in a test sample. The invention also provides method of treatments for diseases or conditions resulting from dysregulations and/or imbalances of the histamine and/or histidine system.

As described herein, the invention provides polypeptides, antibodies and/or antibody fragments engineered for enhanced binding to free histamine and/or histidine that address limitations of previous antibodies against histamine. While the prior art uses antibodies against histamine and/or histidine, those antibodies recognize only protein-bound histamine and have only limited affinity and sensitivity for free histamine since they were raised by conjugating histamine to a large immunogenic protein carrier, such as bovine serum albumin (BSA) or ovalbumin (OVA) via its primary amine group (see, FIGS. 1A-1B). Thus, those antibodies typically perform poorly in the development of immunoassays.

In some embodiments of any of the aspects, the invention provides polypeptides, antibodies and/or antibody fragments engineered for enhanced binding to free histamine.

Histamine was discovered in 1910 by Dale and Laidlaw (1), and it was identified as a mediator of anaphylactic reactions in 1932 (2). Histamine belongs to the biogenic amines and is synthesized by the pyridoxal phosphate (vitamin B-6)-containing 1-histidine decarboxylase (HDC) from the amino acid histidine. It is synthesized by mast cells, basophils, platelets, histaminergic neurons, and enterochromaffine cells, where it is stored intracellularly in vesicles and released on stimulation.

Histamine (11.14 g/mol), also referred to chemically as 2-(1H-Imidazol-4-yl) ethanamine is composed of an imidazole ring and an amino group connected by a chain of two carbon atoms. Histamine is the decarboxylation product of the amino acid histidine and is a potent mediator of numerous biologic reactions. Besides the well-known triggering of degranulation of mast cells by crosslinking of the FcεRI receptor by specific allergens, several other nonimmunologic stimuli, such as neuropeptides, complement factors (ie, C3a and C5a), cytokines, hyperosmolarity, lipoproteins, adenosine, superoxidases, hypoxia, chemical and physical factors (eg, extreme temperatures, traumas), or alcohol and certain food and drugs, may activate mast cells.

Histamine is also associated with local immune responses to foreign pathogens. For example, the granules of mast cells or white blood cells generate and/or store histamine which is released upon injury or exposure to allergens. Histamine also functions as a neurotransmitter and plays a role in the pathways of gastric acid secretion in the stomach.

It is noted that the dysregulation or imbalances of the histamine system can be a leading contributor to a variety of disease states and symptoms, many of which can be debilitating or life-disruptive. Basal plasma histamine concentrations of 0.3 to 1.0 ng/ml are considered normal (3). Histadelia pertains to high blood histamine levels although according to Pfeiffer, the reading must at least be 70 ng/ml to qualify as histadelia. Exemplary diseases and/or conditions include histapenia and/or histadelia. Abnormally high histamine levels can also lead to excessive allergies, hyperactivity, compulsive or obsessive behavior, vertigo, inner ear pressure, depression, anxiety, panic attacks, migraine headaches, heightened emotional sensitivity and/or suicidal tendencies. Reduced histamine levels can lead to depressed metabolism and/or weight gain, paranoia, grandiosity, hallucinations (e.g., classic schizophrenic symptoms), tinnitus, hirsutism, visual and auditory abnormalities, anxiety and food sensitivities. Accordingly, the polypeptides, compositions comprising the same, kits, and analyte detection systems provided herein can be used for medical diagnostics and the early detection of diseases.

Further it is also noted that Histamine poisoning is one example of food poisoning. Histamine is produced from free histidine by means of bacteria having histidine decarboxylase (mainly *Morganella*). Lean fish, such as tuna and mackerel, especially have the high histidine content as the precursor of histamine. Fish meat polluted with such bacteria may have large accumulation of histamine. Uptake of the polluted fish meat causes transient food poisoning. Accordingly, the polypeptides, compositions comprising the same, kits, and analyte detection systems provided herein can be used for food safety applications.

In some embodiments of any of the aspects, the antibody or antigen-binding portion thereof provided herein, is a polypeptide, comprising a variable heavy chain (VH) domain and a variable light chain domain.

Generally, the variable heavy chain domain comprises three complementarity determining regions (CDRs). These CDRs are referred to as variable heavy chain complementarity determining region 1 (VH CDR1), variable heavy chain complementarity determining region 2 (VH CDR2), and variable heavy chain complementarity determining region 3 (VH CDR3).

Amino acid sequence of the VH CDR1 can be selected from an amino acid sequence having at least 85%, 86%, 87%, 88%, 89%, 90%, 91%, 92%, 93%, 94%, 95%, 96%, 97%, 98% or 99% identity to an amino acid sequence selected from the group consisting of: AVALGGNMN (SEQ ID NO: 1) and YSFTGYNMN (SEQ ID NO: 2). For example, the VH CDR 1 comprises an amino acid sequence having at least 90%, 91%, 92%, 93%, 94%, 95%, 96%, 97%, 98% or 99% identity to SEQ ID NO: 1 or SEQ ID NO 2. In some embodiments of the various aspects described herein, the VH CDR 1 comprises an amino acid sequence having at 97%, 98% or 99% identity to SEQ ID NO: 1 or SEQ ID NO 2. In some embodiments of the various aspects described herein, the VH CDR 1 comprises an amino acid sequence having 100% identity to SEQ ID NO: 1 or SEQ ID NO: 2.

In some preferred embodiments, the VH CDR1 comprises an amino acid sequence having at least 85% identity to SEQ ID NO: 2.

Amino acid sequence of the VH CDR2 can be selected from an amino acid sequence having at least 85%, 86%, 87%, 88%, 89%, 90%, 91%, 92%, 93%, 94%, 95%, 96%, 97%, 98% or 99% identity to an amino acid sequence selected from the group consisting of: WIGNIAVAIGLTRY (SEQ ID NO: 3) and WIGNINPYYGSTRY (SEQ ID NO: 4). For example, the VH CDR 2 comprises an amino acid sequence having at least 90%, 91%, 92%, 93%, 94%, 95%, 96%, 97%, 98% or 99% identity to SEQ ID NO: 3 or SEQ ID NO 4. In some embodiments of the various aspects described herein, the VH CDR 2 comprises an amino acid sequence having at 97%, 98% or 99% identity to SEQ ID NO: 3 or SEQ ID NO 4. In some embodiments of the various aspects described herein, the VH CDR 2 comprises an amino acid sequence having 100% identity to SEQ ID NO: 3 or SEQ ID NO: 4.

In some preferred embodiments, the VH CDR2 comprises an amino acid sequence having at least 85% identity to SEQ ID NO: 4.

Generally, the VH CDR3 comprises an amino acid sequence having at least 85%, 86%, 87%, 88%, 89%, 90%, 91%, 92%, 93%, 94%, 95%, 96%, 97%, 98% or 99% identity to an amino acid sequence selected from the group consisting of: RDDDYGEIDYFDY (SEQ ID NO: 5) and RAGVKGNILAAGN (SEQ ID NO: 83). For example, the VH CDR 3 comprises an amino acid sequence having at least 90%, 91%, 92%, 93%, 94%, 95%, 96%, 97%, 98% or 99% identity to SEQ ID NO: 5 or SEQ ID NO: 83. In some embodiments of the various aspects described herein, the VH CDR 3 comprises an amino acid sequence having at 97%, 98% or 99% identity to an amino acid selected from the group consisting of SEQ ID NO: 5 or SEQ ID NO: 83. In some embodiments of the various aspects described herein, the VH CDR 3 comprises an amino acid sequence having 100% identity to SEQ ID NO: 5 or SEQ ID NO: 83.

In some preferred embodiments, the VH CDR2 comprises an amino acid sequence having at least 85% identity to SEQ ID NO: 5.

In some embodiments of any of the aspects, the variable heavy chain domain comprises a VH CDR1 amino acid sequence having at least 85% identity to SEQ ID NO: 1 or SEQ ID NO: 2, and a VH CDR2 amino acid sequence having at least 85% identity to SEQ ID NO: 3 or SEQ ID NO: 4.

In some embodiments of any of the aspects, the variable heavy chain domain comprises a VH CDR1 amino acid sequence having at least 85% identity to SEQ ID NO: 1 or SEQ ID NO: 2, and a VH CDR3 amino acid sequence having at least 85% identity to SEQ ID NO: 5 or SEQ ID NO: 83.

In some embodiments of any of the aspects, the variable heavy chain domain comprises a VH CDR2 amino acid sequence having at least 85% identity to SEQ ID NO: 3 or SEQ ID NO: 4, and a VH CDR3 amino acid sequence having at least 85% identity to SEQ ID NO: 5 or SEQ ID NO: 83.

In some preferred embodiments of any of the aspects, the variable heavy chain domain comprises a VH CDR1 amino acid sequence having at least 85% identity to SEQ ID NO: 2, a VH CDR2 amino acid sequence having at least 85% identity to SEQ ID NO: 4, and a VH CDR3 amino acid sequence having at least 85% identity to SEQ ID NO: 5.

Similar to the variable heavy chain domain, the variable light chain domain comprises three complementarity determining regions. The CDRs of the variable light chain domain are referred to as variable light chain complementarity determining region 1 (VL CDR1), variable light chain complementarity determining region 2 (VL CDR2), and variable light chain complementarity determining region 3 (VL CDR3).

Amino acid sequence of the VL CDR1 can be selected from an amino acid sequence having at least 85%, 86%, 87%, 88%, 89%, 90%, 91%, 92%, 93%, 94%, 95%, 96%, 97%, 98% or 99% identity to an amino acid sequence selected from the group consisting of: QSIVHSNGNTYLE (SEQ ID NO: 6), QSLVHSGGNTYLE (SEQ ID NO: 7), QSIVHSSGNTYLE (SEQ ID NO: 8), QSLVHSSGNTYLE (SEQ ID NO: 9), QSIVHSGGNTYLE (SEQ ID NO: 10), QTIVHSNGNTYLE (SEQ ID NO: 11), QSIVHSDGNTYLE (SEQ ID NO: 12), QSIVSSSGNTYLE (SEQ ID NO: 13), QSIVYSDGNTYLE (SEQ ID NO: 14), QTIVHSSGNTYLE (SEQ ID NO: 15), QSIVHRDGNTYLE (SEQ ID NO: 16), QSLVHSDGNTYLE (SEQ ID NO: 17), QTIVHSNGNTYLE (SEQ ID NO: 18), GVAGANAGAGALA (SEQ ID NO: 19), and QSIVYSSGNTYLE (SEQ ID NO: 20). For example, the VL CDR 1 comprises an amino acid sequence having at least 90%, 91%, 92%, 93%, 94%, 95%, 96%, 97%, 98% or 99% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 or SEQ ID NO: 20. In some embodiments of the various aspects described herein, the VL CDR 1 comprises an amino acid sequence having at 97%, 98% or 99% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 or SEQ ID NO: 20. In some embodiments of the various aspects described herein, the VL CDR 1 comprises an amino acid sequence having 100% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 or SEQ ID NO: 20.

In some embodiments, the VL CDR 1 comprises an amino acid sequence having at least 85% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or SEQ ID NO: 19.

In some embodiments, the VL CDR1 comprises an amino acid sequence having at least 85% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18.

In some preferred embodiments, the VL CDR1 comprises an amino acid sequence having at least 85% identity to SEQ ID NO: 6.

Amino acid sequence of the VL CDR2 can be selected from an amino acid sequence having at least 85%, 86%, 87%, 88%, 89%, 90%, 91%, 92%, 93%, 94%, 95%, 96%, 97%, 98% or 99% identity to an amino acid sequence selected from the group consisting of: LLIYAVKATGA (SEQ ID NO: 21), LLIYKVSNRFS (SEQ ID NO: 22). For example, the VL CDR 2 comprises an amino acid sequence having at least 90%, 91%, 92%, 93%, 94%, 95%, 96%, 97%, 98% or 99% identity to SEQ ID NO: 21 or SEQ ID NO 22. In some embodiments of the various aspects described herein, the VL CDR 2 comprises an amino acid sequence having at 97%, 98% or 99% identity to SEQ ID NO: 21 or SEQ ID NO 22. In some embodiments of the various aspects described herein, the VL CDR 2 comprises an amino acid sequence having 100% identity to SEQ ID NO: 21 or SEQ ID NO: 22.

In some preferred embodiments, the VL CDR2 comprises an amino acid sequence having at least 85% identity to SEQ ID NO: 22.

Amino acid sequence of the VL CDR3 can be selected from an amino acid sequence having at least 85%, 86%, 87%, 88%, 89%, 90%, 91%, 92%, 93%, 94%, 95%, 96%, 97%, 98% or 99% identity to an amino acid sequence selected from the group consisting of: SQATHVPY (SEQ ID NO: 23), AGAVAVAA (SEQ ID NO: 24) and FQASHVPY (SEQ ID NO: 25). For example, the VL CDR 3 comprises an amino acid sequence having at least 90%, 91%, 92%, 93%, 94%, 95%, 96%, 97%, 98% or 99% identity to SEQ ID NO: 23, SEQ ID NO: 24 or SEQ ID NO 25. In some embodiments of the various aspects described herein, the VL CDR3 comprises an amino acid sequence having at 97%, 98% or 99% identity to SEQ ID NO: 23, SEQ ID NO: 24 or SEQ ID NO 25. In some embodiments of the various aspects described herein, the VL CDR3 comprises an amino acid sequence having 100% identity to SEQ ID NO: 23, SEQ ID NO: 24 or SEQ ID NO 25.

In some preferred embodiments, the VL CDR3 comprises an amino acid sequence having at least 85% identity to SEQ ID NO: 25.

In some embodiments of any of the aspects, the variable heavy chain domain comprises a VL CDR1 amino acid sequence having at least 85% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 or SEQ ID NO: 20, and a VL CDR2 amino acid sequence having at least 85% identity to SEQ ID NO: 21 or SEQ ID NO: 22.

In some embodiments of any of the aspects, the variable heavy chain domain comprises a VL CDR1 amino acid sequence having at least 85% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or SEQ ID NO: 19, and a VL CDR2 amino acid sequence having at least 85% identity to SEQ ID NO: 21 or SEQ ID NO: 22.

In some embodiments of any of the aspects, the variable heavy chain domain comprises a VL CDR1 amino acid sequence having at least 85% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18, and a VL CDR2 amino acid sequence having at least 85% identity to SEQ ID NO: 21 or SEQ ID NO: 22.

In some embodiments of any of the aspects, the variable heavy chain domain comprises a VL CDR1 amino acid sequence having at least 85% identity to SEQ ID NO: 6, and a VL CDR2 amino acid sequence having at least 85% identity to SEQ ID NO: 22.

In some embodiments of any of the aspects, the variable heavy chain domain comprises a VL CDR1 amino acid sequence having at least 85% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 or SEQ ID NO: 20, and a VL CDR3 amino acid sequence having at least 85% identity to SEQ ID NO: 23, SEQ ID NO: 24 or SEQ ID NO: 25.

In some embodiments of any of the aspects, the variable heavy chain domain comprises a VL CDR1 amino acid sequence having at least 85% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or SEQ ID NO: 19, and a VL CDR3 amino acid sequence having at least 85% identity to SEQ ID NO: 23, SEQ ID NO: 24 or SEQ ID NO: 25.

In some embodiments of any of the aspects, the variable heavy chain domain comprises a VL CDR1 amino acid sequence having at least 85% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18, and a VL CDR3 amino acid sequence having at least 85% identity to SEQ ID NO: 23, SEQ ID NO: 24 or SEQ ID NO: 25.

In some embodiments of any of the aspects, the variable heavy chain domain comprises a VL CDR1 amino acid sequence having at least 85% identity to SEQ ID NO: 6, and a VL CDR3 amino acid sequence having at least 85% identity to SEQ ID NO: 25.

In some embodiments of any of the aspects, the variable heavy chain domain comprises a VL CDR2 amino acid sequence having at least 85% identity to SEQ ID NO: 21 or SEQ ID NO: 22, and a VL CDR3 amino acid sequence having at least 85% identity to SEQ ID NO: 23, SEQ ID NO: 24 or SEQ ID NO: 25.

In some embodiments of any of the aspects, the variable heavy chain domain comprises a VL CDR2 amino acid sequence having at least 85% identity to SEQ ID NO: 22, and a VL CDR3 amino acid sequence having at least 85% identity to SEQ ID NO: 25.

In some preferred embodiments of any of the aspects, the variable heavy chain domain comprises a VL CDR1 amino acid sequence having at least 85% identity to SEQ ID NO: 6, a VL CDR2 amino acid sequence having at least 85% identity to SEQ ID NO: 22, and a VL CDR3 amino acid sequence having at least 85% identity to SEQ ID NO: 25.

In some embodiments of any of the aspects, the VH CDR1 comprises an amino acid sequence having at least 85% identity to SEQ ID NO: 1 or SEQ ID NO: 2; the VH CDR2 comprises an amino acid sequence having at least 85% identity to SEQ ID NO: 3 or SEQ ID NO: 4; the VH CDR3 comprises an amino acid sequence having at least 85% identity SEQ ID NO: 5; the VL CDR1 comprises an amino acid sequence having at least 85% identity SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 or SEQ ID NO: 20; VL CDR2 comprises an amino acid sequence having at least 85% identity to SEQ ID NO: 21 or SEQ ID NO: 22; and the VLCDR3 comprises an amino acid sequence having at least 85% identity to SEQ ID NO: 23, SEQ ID NO: 24 or SEQ ID NO: 25.

In some embodiments of any of the aspects, the VL CDR1 comprises an amino acid sequence having at least 85% identity to the amino acid sequence QSIVHSNGNTYLE (SEQ ID NO: 6), the VL CDR2 comprises an amino acid sequence having at least 85% identity to the amino acid sequence LLIYKVSNRFS (SEQ ID NO: 22), and the VL CDR3 comprises an amino acid sequence having at least 85% identity to the amino acid sequence FQASHVPY (SEQ ID NO: 25).

In some embodiments of any of the aspects, the VH CDR1 comprises an amino acid sequence having at least 85% identity to SEQ ID NO: 2; the VH CDR2 comprises an amino acid sequence having at least 85% identity to SEQ ID NO: 4; and the VH CDR3 comprises an amino acid sequence having at least 85% identity to SEQ ID NO: 5; the VL CDR1 comprises an amino acid sequence having at least 85% identity to SEQ ID NO: 6, the VL CDR2 comprises an amino acid sequence having at least 85% identity to SEQ ID NO: 22, and the VL CDR3 comprises an amino acid sequence having at least 85% identity to SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 7, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 20, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 9, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 10, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 11, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 23.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 12, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 13, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 14, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 15, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 16, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 17, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 18, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 19, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 3, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 19, the VL CDR2 comprises an amino acid sequence having at least 85% identity to the amino acid sequence of SEQ ID NO: 21, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 20, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 20, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 24.

In some embodiments of any of the aspects, the VH CDR1 comprises an amino acid sequence having at least 85% identity to the amino acid sequence of SEQ ID NO: 1, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 20, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 3, and the VH CDR3 comprises an amino acid sequence having at least 85% identity to the amino acid sequence of SEQ ID NO: 5; the VL CDR1 comprises an amino acid sequence having at least 85% identity to the amino acid sequence of SEQ ID NO: 20, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

In some embodiments of any of the aspects, the VH CDR1 comprises an amino acid sequence having at least 85% identity to the amino acid sequence of SEQ ID NO: 2, the VH CDR2 comprises an amino acid sequence having at least 85% identity to the amino acid sequence of SEQ ID NO: 4, and the VH CDR3 comprises an amino acid sequence having at least 85% identity to the amino acid sequence of SEQ ID NO: 83, the VL CDR1 comprises an amino acid sequence having at least 85% identity to the amino acid sequence of SEQ ID NO: 20, the VL CDR2 comprises an amino acid sequence having at least 85% identity to the amino acid sequence of SEQ ID NO: 22, and the VL CDR3 comprises an amino acid sequence having at least 85% identity to the amino acid sequence of SEQ ID NO: 25.

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., Biochem. 32:1180-1187 (1993); Kobayashi et al. Protein Eng. 12(10): 879-884 (1999); and Burks et al. Proc. Natl. Acad. Set USA 94:412-417 (1997)). Near et al. Mol. Immunol. 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2). Thus, the invention also includes, in certain embodiments, variable amino acid sequences having at least 85% identity to those sequences disclosed herein.

It is noted that the VH and VL domains can be oriented in any desired direction in the polypeptide. For example, the VL domain can be linked to the N-terminus of the VH domain. Alternatively, the VL domain can be linked to the C-terminus of the VH domain.

In some embodiments of any of the aspects, the polypeptide comprises a linker between the VH domain and the VL domain. The linker can be a chemical linker, a single peptide bond (e.g., linked directly to each other) or a peptide linker containing one or more amino acid residues (e.g. with an intervening amino acid or amino acid sequence between the VH domain and the VL domain).

In some embodiments of any of the aspects, the linker used to link the two domains is a flexible linker. As used herein, a “flexible linker” is a linker which does not have a fixed structure (secondary or tertiary structure) in solution and is therefore free to adopt a variety of conformations. Generally, a flexible linker has a plurality of freely rotating bonds along its backbone. In contrast, a rigid linker is a linker which adopts a relatively well-defined conformation when in solution. Rigid linkers are therefore those which have a particular secondary and/or tertiary structure in solution.

In some embodiments of the various aspects described herein, the VH domain and the VL domain are linked via a peptide linker. The term “peptide linker” as used herein denotes a peptide with amino acid sequences, which is in some embodiments of synthetic origin. It is noted that peptide linkers may affect folding of a given fusion protein, and may also react/bind with other proteins, and these properties can be screened for by known techniques. A peptide linker can comprise 1 amino acid or more, 5 amino acids or more, 10 amino acids or more, 15 amino acids or more, 20 amino acids or more, 25 amino acids or more, 30 amino acids or more, 35 amino acids or more, 40 amino acids or more, 45 amino acids or more, 50 amino acids or more and beyond. Conversely, a peptide linker can comprise less than 50 amino acids, less than 45 amino acids, less than 40 amino acids, less than 35 amino acids, less than 30 amino acids, less than 30 amino acids, less than 25 amino acids, less than 20 amino acids, less than 15 amino acids or less than 10 amino acids.

In some embodiments of the various aspects described herein, the peptide linker comprises from about 5 amino acids to about 40 amino acids. For example, the peptide linker can comprise from about 5 amino acids to about 35 amino acids, from about 10 amino acids to 30 amino acids, or from about 10 amino acids to about 25 amino acids.

In some embodiments of the various aspects described herein, the linker comprises 10, 11, 12, 13, 14, 15, 16, 17, 18, 19, 20, 21, 22, 23, 24 or 25 amino acids. For example, the linker comprises 10, 11, 12, 13, 14, 15, 16, 17, 18, 19 or 20 amino acids. Preferably, the linker comprises 12, 13, 14, 15, 16, 17 or 18 amino acids. More preferably, the linker comprises 14, 15 or 16 amino acids. In some embodiments of the various aspects described herein, the linker comprises 15 amino acids.

In some embodiments of any of the aspects, the linker comprises an amino acid sequence having at least 85% identity to the amino acid sequence EGKSSGSGSESKAS (SEQ ID NO: 26).

Additional exemplary peptide linkers include those that consist of glycine and serine residues, the so-called Gly-Ser polypeptide linkers. As used herein, the term “Gly-Ser polypeptide linker” refers to a peptide that consists of glycine and serine residues. In some embodiments of the various aspects described herein, the peptide linker comprises the amino acid sequence (GlyxSer) n, where x is 2, 3, 4, 5 or 6, and n is 1, 2, 3, 4, 5, 6, 7, 8, 9 or 10, e.g., SEQ ID NOs: 27-76. In some embodiments of the various aspects described herein, x is 3 and n is 3, 4, 5 or 6. In some embodiments of the various aspects described herein, x is 3 and n is 4 or 5. In some embodiments of the various aspects described herein, x is 4 and n is 3, 4, 5 or 6. In some embodiments of the various aspects described herein, x is 4 and n is 4 or 5. In some embodiments of the various aspects described herein, x is 3 and n is 2. In some embodiments of the various aspects described herein, x is 3 or 4 and n is 1.

More exemplary linkers, in addition to those described herein, include a string of histidine residues, e.g., His6 ((HHHHHH (SEQ ID NO: 77)); sequences made up of Ala and Pro, varying the number of Ala-Pro pairs to modulate the flexibility of the linker; and sequences made up of charged amino acid residues e.g., mixing Glu and Lys. Flexibility can be controlled by the types and numbers of residues in the linker. See, e.g., Perham, 30 Biochem. 8501 (1991); Wriggers et al., 80 Biopolymers 736 (2005).

In some embodiments of the various aspects described herein, the linker can be a chemical linker. Chemical linkers can comprise a direct bond or an atom such as oxygen or sulfur, a unit such as NH, C(O), C(O) NH, SO, $SO_2$, $SO_2NH$, or a chain of atoms, such as substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{12}$ aryl, substituted or unsubstituted $C_5$-$C_{12}$ heteroaryl, substituted or unsubstituted $C_5$-$C_{12}$ heterocyclyl, substituted or unsubstituted $C_3$-$C_{12}$ cycloalkyl, where one or more methylenes can be interrupted or terminated by O, S, S(O), $SO_2$, NH, or C(O).

In some embodiments of any of the aspects, the polypeptide further comprises a Fc region of an immunoglobulin, i.e., the polypeptide further comprises an Fc domain. The Fc domain can be located at the N-terminus or C-terminus of the polypeptide. In some embodiments of any of the aspects, the Fc domain is at the N-terminus of the polypeptide. In some other embodiments of any of the aspects, the Fc domain is at the C-terminus of the polypeptide.

As used herein, an "Fc region" or "Fc element" is a protein sequence that comprises at least a CH3 domain of an IgG antibody element, and more preferably a CH2 and CH3 domain, and in some cases a hinge region as well. The following are typical Fc regions that are useful in constructing fusion proteins and that consist of a few amino acids from the CH1 domain, a hinge region, a CH2 domain, and a CH3 domain. Fc regions are related to each other through sequence similarity, and are defined herein as sequences that can be aligned using BLAST (https://blast.ncbi.nlm.nih.gov/Blast.cgi) with one of the sequences below to give an "Expect" score of at most 1e-100 (with lower scores indicating greater similarity).

Generally, the "Fc domain" is the polypeptide comprising the constant region of an antibody excluding the first constant region immunoglobulin domain and in some cases, part or all of the hinge. Thus, an Fc domain refers to the non-antigen binding portion of an antibody, whether in monomeric or multimeric form. The Fc domain can be from any vertebrate source, including mammals such as primates (e.g., humans), non-human primates (e.g. Chimpanzee, Macaque) and rodents (e.g. a mouse, rat, rabbit, guinea pig). Preferably, the antibody from which the Fc domain arises is of human origin.

An Fc domain includes the hinge region of the heavy chain. By "hinge" or "hinge region" or "antibody hinge region" or "immunoglobulin hinge region" herein is meant the flexible polypeptide comprising the amino acids between the first and second constant domains of an antibody, just upstream of the papain cleavage. Accordingly, for IgG, an Fc domain comprises immunoglobulin domains CH2 and CH3 and the hinge region between CH1 and CH2. Although the boundaries of the Fc region may vary, the human IgG heavy chain Fc region is usually defined to include residues C226 or P230 to its carboxyl-terminus, wherein the numbering is according to the EU index and in Kabat. In some embodiments, as is more fully described below, amino acid modifications are made to the Fc domain, for example to alter binding to one or more FcγR receptors or to the FcRn receptor.

Accordingly, in certain embodiments, the term Fc domain includes the hinge region which may be truncated, modified by replacement, deletion and/or insertion and further the modified or unmodified hinge region may be the site of attachment of a linker domain.

An "analog of an Fc domain" refers to a molecule or sequence that is modified from the native Fc but still comprises a binding site for the salvage receptor. The term analog of an Fc domain includes a molecule or sequence that is humanized from a non-human native Fc. The term analog of an Fc domain also includes a molecule or sequence that lacks, or has modifications of, one or more native Fc residues that affect or are involved in disulfide formation, incompatibility with a host cell, N-terminal heterogeneity upon expression, stability, glycolsylation, interaction with a complement, binding to an Fc salvage receptor and/or interaction with an Fcγ receptor.

The terms "fragments of the Fc domain" or "fragment of the Fc domain" refers to a native Fc from which one or more sites have been removed where the removed site(s) does not constitute structural features or functional activity that is required by the fusion proteins of the present invention. Fragments of the Fc domain include deleting residues from the native Fc or truncating the native Fc and may include substitutions of the remaining residues. The inserted or altered residues (e.g., the substituted residues) may be natural amino acids or altered amino acids, peptidomimetics, unnatural amino acids, or D-amino acids.

Generally, the Fc domain includes a sequence at least 80%, 81%, 82%, 83%, 84%, 85%, 86%, 87%, 88%, 89%, 90%, 91%, 92%, 93%, 94%, 95%, 96%, 97%, 98%, or 99% identical to IgG1, IgG2, IgG3, IgG4, IgD, IgA, IgE, or IgM, in particular human IgG1 or IgG3.

The term Fc domain encompasses native Fc and analogs of Fc and includes monomeric and multimeric forms whether prepared by a digest of an intact antibody or produced by other means.

In some embodiments, the Fc domain comprises at least a hinge domain (upper, middle, and/or lower hinge region), a CH2 domain (or a variant or fragment thereof), and a CH3 domain (or a variant or fragment thereof). In some embodiments, the Fc domain consists of a hinge domain (upper, middle, and/or lower hinge region), a CH2 domain (or a variant or fragment thereof), and a CH3 domain (or a variant or fragment thereof). In some embodiments, the Fc domain consists of a hinge domain (upper, middle, and/or lower hinge region), a CH2 domain (or a variant or fragment thereof), a CH3 domain (or a variant or fragment thereof), and a CH4 domain (or a variant or fragment thereof). In some embodiments, the Fc domain consists of a hinge domain (upper, middle, and/or lower hinge region) and a CH2 domain. In some embodiments, the Fc domain consists of a hinge domain (upper, middle, and/or lower hinge region) and a CH3 domain (or a variant or fragment thereof).

In some embodiments, the Fc domain consists of a CH2 domain (or a variant or fragment thereof), and a CH3 domain (or a variant or fragment thereof). In some embodiments, the Fc domain consists of a complete CH2 domain and a complete CH3 domain. In some embodiments, the Fc domain consists of a complete CH2 domain and a complete CH3 domain. In some embodiments, the Fc domain comprises at least the portion of an Fc molecule known in the art to be required for FcRn binding. In some embodiments, the Fc domain comprises at least the portion of an Fc molecule known in the art to be required for FcγR binding. In some embodiments, the Fc domain comprises at least the portion of an Fc molecule known in the art to be required for Protein A binding. In some embodiments, the Fc domain comprises at least the portion of an Fc molecule known in the art to be required for Protein G binding.

As described herein, an Fc domain generally refers to a polypeptide comprising all or part of the Fc domain of an immunoglobulin heavy-chain. As discussed above, this includes, but is not limited to polypeptides comprising the entire hinge region, CH1, CH2, and/or CH3 domains as well as fragments of such peptides comprising, for example, the hinge, CH2 and CH3 domains. The Fc domain may be derived from any immunoglobulin of any species and/or subtype, including but not limited to, a human IgG1, IgG2, IgG3, IgG4, IgD, IgA, IgE, or IgM antibody. The Fc domain includes the last two constant region immunoglobulin domains of IgA, IgD, and IgG, the last three constant region immunoglobulin domains of IgE and IgM, and the flexible hinge N-terminal to these domains. For IgA and IgM, Fc may include the J chain.

The Fc domain as used herein encompasses native Fc and Fc variant molecules. As with the Fc variants and native Fc proteins, the term Fc domain includes molecules in monomeric and multimeric form, whether digested from an antibody or produced by other means.

It is noted that any Fc domain may be modified such that it varies in amino acid sequence from the native Fc domain of a naturally occurring immunoglobulin molecule. In some embodiments, the Fc domain retains an effector function, for example, FcRN and/or FcγR binding.

In those embodiments where the polypeptides described herein comprise an Fc domain, modifications, such as amino acid substitutions, can be introduced to modulate, i.e., increase or decrease, one or more functions or properties mediated by the Fc domain. Such mutations or substitutions include those that, for example, promote heterodimerization s, promote or increase serum half-life, and/or modify various Fc effector functions.

Fc effector functions refer to the biological activities of an antibody that are not mediated by the binding of the heavy and light variable regions to a target antigen, but by other regions or portions of the antibody, particularly the Fc region. Examples of such antibody effector functions include C1q binding and complement dependent cytotoxicity; Fc receptor binding; antibody-dependent cell-mediated cytotoxicity (ADCC); antibody-dependent cellular phagocytosis (ADCP); down regulation of cell surface receptors (e.g., B cell receptor); lack of activation of platelets that express Fc receptor; B cell activation; and increased serum half-life.

For example, various methods are known in the art that increase desired pairing of Fc-containing polypeptide chains to produce preferred asymmetric fusion proteins at acceptable yields (see, for example, Klein et al. (2012) mAbs 4:653-663; and Spiess et al. (2015) Molecular Immunology 67(2PartA): 95-106). Methods to obtain desired pairing of Fc-containing polypeptides include, but are not limited to, charge-based pairing (electrostatic steering), "knobs-into-holes" steric pairing, SEEDbody pairing, and leucine zipper-based pairing (See, for example, Ridgway et al. (1996) Protein Eng. 9:617-621; Merchant et al. (1998) Nat. Biotech. 16:677-681; Davis et al. (2010) Protein Eng. Des. Sel. 23:195-202; Gunasekaran et al. (2010) J. Biol. Chem. 285: 19637-19646; Wranik et al. (2012) J. Biol. Chem. 287: 43331-43339; U.S. Pat. No. 5,932,448; and PCT Publication Nos. WO 1993/011162, WO 2009/089004, and WO 2011/034605, the contents of each of which are herein incorporated by reference in their entireties). Accordingly, in some embodiments, where Fc domains can be used to assist in the formation of stable multivalent constructs, such as, for example, a divalent, trivalent or tetravalent constructs.

In some embodiments, a mutation or substitution is present in a CH3 domain of the Fc region (See, e.g., Xu et al. (2015) mAbs 7 (1): 231-42). For example, the IgG1 CH3 domain interface comprises four unique charge residue pairs involved in domain-domain interactions: D356-K439', E357-K370', K392-D399', and D399-K409', where residue numbering in the second chain is indicated by ('), and the amino acid numbering is according to the EU numbering scheme of Kabat. Due to the 2-fold symmetry present in endogenous CH3-CH3 domain interactions, each unique interaction is represented twice in the structure (e.g., D399-K409' and K409-D399'). In the endogenous, wild-type sequence, K409-D399' favors both heterodimer and homodimer formation. However, a single mutation switching the charge polarity (e.g., K409E; positive to negative charge) in the first chain leads to unfavorable interactions for the formation of the first chain homodimer. The unfavorable interactions arise due to the repulsive interactions occurring between the same charges (negative-negative; K409E-D399' and D399-K409E'). A similar mutation switching the charge polarity (D399K'; negative to positive) in the second chain leads to unfavorable interactions (K409'-D399K' and D399K-K409') for the second chain homodimer formation. But, at the same time, these two mutations (K409E and D399K') lead to favorable interactions (K409E-D399K' and D399-K409') for the heterodimer formation. The electrostatic steering effect on heterodimer formation and homodimer discouragement can be further enhanced by mutation of additional charge residues which may or may not be paired with an oppositely charged residue in the second chain including, for example, R355 and K360 (See, e.g., PCT Publication No. WO 2016/164089). Accordingly, in some embodiments of the polypeptides described herein, amino acid substitutions, deletions, and/or additions can be introduced to an Fc domain promote heterodimerization of Fc domains. In some such embodiments, the substitutions comprise K409E and D399K'.

In some embodiments, an Fc domain being used in the polypeptides described herein can be modified to enhance serum half-life. Fc domains comprising one or more mutations that enhance or diminish antibody binding to the Fc receptor, e.g., at acidic pH as compared to neutral pH, are known in the art. For example, the polypeptides disclosed herein can comprise one or more mutations in the $C_H2$ or a $C_H3$ region of the Fc domain, such that the mutation(s) increases the affinity of the Fc domain to FcRn in an acidic environment (e.g., in an endosome where pH ranges from about 5.5 to about 6.0). Such mutations may result in an increase in serum half-life of the construct when administered to an animal. Methods of modifying the Fc domain for desired characteristics, such as enhanced serum half-life are known in the art.

In some embodiments of any of the aspects, the Fc region of an immunoglobulin is a human IgG Fc region.

In certain embodiments, the polypeptide has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG2 (e.g., human IgG1 or IgG2). In some embodiments, the heavy chain constant region is human IgG1. In some embodiments, the polypeptide has a light chain constant region chosen from, e.g., the light chain constant regions of kappa or lambda, in some embodiments kappa (e.g., human kappa). In some embodiments, the constant region is altered, e.g., mutated, to modify the properties of the polypeptide molecule (e.g., to increase or decrease one or more of: Fc receptor binding, antibody glycosylation, the number of cysteine residues, effector cell function, or complement function).

The polypeptide described herein can be in form of a full antibody or a fragment thereof, e.g., a Fab, F(ab')2, Fv, or a single chain Fv fragment (scFv). For example, the polypeptide can be selected from the group consisting of Fv, Fab, Fab', F(ab)2, F(ab')2, single-chain antibody, single-chain antibody (scFV), sc(Fv)2, monovalent antibody lacking hinge region, whole antibody, disulfide-stabilized Fv (dsFv), diabody dAb, a bivalent or bispecific antibody.

In certain embodiments, the polypeptide is a monoclonal antibody or an antibody with single specificity. The polypeptide can also be a humanized, chimeric, camelid, shark, or in vitro-generated antibody or a fragment thereof. In some embodiments, the polypeptide is a humanized antibody. The term "antibody", as used herein, refers to a class of structurally related proteins generally comprising two pairs of polypeptide chains: one pair of light (L) chains and one pair of heavy (H) chains. In an intact, endogenous immunoglobulin, all four of these chains are interconnected by disulfide bonds. The structure of immunoglobulins has been well characterized. See, e.g., Paul (2013) *Fundamental Immunology* 7th ed., Ch. 5, Lippincott Williams & Wilkins, Philadelphia, PA. Briefly, each heavy chain typically comprises a heavy chain variable region ($V_H$) and a heavy chain constant region ($C_H$). The heavy chain constant region typically comprises three domains, $C_{H1}$, $C_{H2}$, and $C_{H3}$. Each light chain typically comprises a light chain variable region ($V_L$) and a light chain constant region ($C_L$). The light chain constant region typically comprises one domain. An antibody, as used herein, typically refers to intact antibodies (e.g., intact immunoglobulins).

The antibody can be a monospecific antibody. The term "monospecific antibody" refers to an antibody that displays a single binding specificity and affinity for a particular target, i.e., histamine.

The heavy and light chains of the antibody can be full-length (e.g., an antibody can include at least one or at least two complete heavy chains, and at least one or at least two complete light chains) or can include an antigen-binding fragment (e.g., a Fab, F(ab')2, Fv, a single chain Fv fragment, a single domain antibody, a diabody (dAb), a bivalent or bispecific antibody or fragment thereof, a single domain variant thereof, or a camelid antibody).

Accordingly, in some embodiments of any of the aspects, the polypeptide is a single-chain antibody. A single-chain antibody (scFv) is an antibody in which a VL and a VH region are joined via a linker {e.g., a synthetic sequence of amino acid residues) to form a continuous protein chain wherein the linker is long enough to allow the protein chain to fold back onitself and form a monovalent antigen binding site or they can form multimers (e.g., dimers, trimers, or tetramers), depending on the length of a flexible linker between the two variable domains. See for example, Bird et al., 1988, Science 242:423-26 and Huston et al., 1988, Proc. Natl. Acad. Sci. USA 85:5879-83, Kortt et al., 1997, Prot. Eng. 10:423; Kortt et al., 2001, Biomol. Eng. 18:95-108).

In some embodiments of any of the aspects, the polypeptide can be a single domain antibody. Single domain antibodies can include antibodies whose complementary determining regions are part of a single domain polypeptide. Examples include, but are not limited to, heavy chain antibodies, antibodies naturally devoid of light chains, single domain antibodies derived from conventional four-chain antibodies, engineered antibodies and single domain scaffolds other than those derived from antibodies. Single domain antibodies can be derived from any species including, but not limited to, mouse, human, camel, llama, fish, shark, goat, rabbit, and bovine.

In some embodiments of any of the aspects, the polypeptide is a diabody. Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites, e.g., one for histamine and one for something other than histamine. Similarly, tribodies and tetrabodies are antibodies comprising three and four polypeptide chains, respectively, and forming three and four antigen binding sites, respectively, which can be the same or different.

In certain embodiments, the polypeptide is in the form of a bispecific or multispecific antibody molecule. In one embodiment, the bispecific antibody molecule has a first binding specificity to histamine and a second binding specificity to a different antigen.

In some embodiments, a polypeptide described here is a fully human antibody. In some embodiments, the antibody or antigen-binding portion thereof, is a humanized antibody or antibody agent. In some embodiments, the antibody or antigen-binding portion thereof, is a fully humanized antibody or antibody agent. In some embodiments, the antibody or antigen-binding portion thereof, is a chimeric antibody or antibody agent. In some embodiments, the antibody or antigen-binding portion thereof, is a recombinant polypeptide.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies can contain amino acid residues not encoded by human germ line immunoglobulin sequences (for example, mutations which have been introduced by random or site-specific mutagenesis in vitro or by somatic mutation in vivo), for example in the CDRs, and in particular in CDR3. Recombinant human antibodies as described herein have variable regions and can also contain constant regions derived from immunoglobulin sequences of the human germ line (see Kabat, E. A., et al. (1991). According to particular embodiments, however, such recombinant human antibodies are subjected to in vitro mutagenesis (or to a somatic in vivo mutagenesis, if an animal is used which is transgenic due to human Ig sequences) so that the amino acid sequences of the VH and VL regions of the recombinant antibodies are sequences which, although related to or derived from VH and VL sequences of the human germ line, do not naturally exist within the human antibody germ line repertoire. According to particular embodiments, recombinant antibodies of this kind are the result of selective mutagenesis, such as affinity maturation, or back mutation or of both. Preferably, mutagenesis leads to an affinity to the target which is greater, and/or an affinity to non-target structures which is smaller than that of the parent antibody. A human antibody is one that possesses an amino acid sequence corresponding to that of an antibody produced by a human or a human cell, or derived from a non-human source that utilizes a human antibody repertoire or human antibody-encoding sequences (e.g., obtained from human sources, genetically modified non-human sources or designed de novo).

A humanized or fully human form of the antibody can also be prepared in accordance with methods well known in the art (see e. g. U.S. Pat. No. 5,565,332 to Winter). Humanization can be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions, i.e., the residues critical for the antibody-antigen interaction, onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling).

Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions can also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions can also be generated by isolating Fv clone variable region sequences selected from human-derived display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991). Various display technologies and libraries derived from such technologies are known in the art, e.g., phage display technologies, bacterial display, yeast surface display, eukaryotic viral display, mammalian cell display, and cell-free (e.g., ribosomal display) antibody screening techniques (see, e.g., Etz et al. (2001) J Bacteriol 183:6924-6935; Cornelis (2000) Curr Opin Biotechnol 11:450-454; Klemm et al. (2000) Microbiology 146:3025-3032; Kieke et al. (1997) Protein Eng 10:1303-1310; Yeung et al. (2002) Biotechnol Prog 18:212-220; Boder et al. (2000) Methods Enzymology 328:430-444; Grabherr et al. (2001) Comb Chem High Throughput Screen 4:185-192; Michael et al. (1995) Gene Ther 2:660-668; Pereboev et al. (2001) J Virol 75:7107-7113; Schaffitzel et al. (1999) J Immunol Methods 231:119-135; and Hanes et al. (2000) Nat Biotechnol 18:1287-1292). Methods for identifying antibodies and antigen-binding portions thereof for use in the constructs described herein using various phage display methods are known in the art. In some embodiments, the phage display antibody libraries can be generated using mRNA collected from B cells from immunized mammals. For example, a splenic cell sample comprising B cells can be isolated from mice immunized with a target immune inhibitor receptor polypeptide. mRNA can be isolated from the cells and converted to cDNA using standard molecular biology techniques. See, e.g., Sambrook et al. (1989) "Molecular Cloning: A Laboratory Manual, 2nd Edition," Cold Spring Harbor Laboratory Press, Cold Spring Harbor, N.Y.; Harlow and Lane (1988), supra; Benny K. C. Lo (2004), supra; and Borrebaek (1995), supra. The cDNA coding for the variable regions of the heavy chain and light chain polypeptides of immunoglobulins are used to construct the phage display library. Methods for generating such a library are described in, e.g., Merz et al. (1995) J Neurosci Methods 62 (1-2): 213-9; Di Niro et al. (2005) Biochem J 388 (Pt 3): 889-894; and Engberg et al. (1995) Methods Mol Biol 51:355-376.

In some embodiments of any of the aspects, the polypeptide can be in form of: (i) a Fab fragment, a monovalent fragment made up of the VL, VH, CL and CH1 domains; (ii) a F(ab')2 fragment, a bivalent fragment including two Fab fragments linked by a disulfide bridge at the hinge region; (iii) an Fd fragment made up of the VH and CH1 domains; (iv) an Fv fragment made up of the VL and VH domains of a single arm of an antibody; or (v) a dAb fragment made up of a VH or VL domain (Ward et al., (1989) Nature 341:544-546; which is incorporated by reference herein in its entirety).

It is noted that antibodies are classified into five main classes or isotypes—IgA, IgD, IgE, IgG and IgM. Accordingly, in some embodiments of any of the aspects, the polypeptide is an antibody selected from the group consisting of IgA isotype, IgD isotype, IgG isotype, IgE isotype and IgM isotype.

The isotypes can be further divided into subclasses. For example, IgG consists of four human subclasses (IgG1, IgG2, IgG3 and IgG4), which are highly homologous and differ mainly in the hinge region and the extent to which they activate the host immune system. IgG1 and IgG4 contain two inter-chain disulphide bonds in the hinge region, IgG2 has 4 and IgG3 has 11. In mice the IgG class is divided into five sub-classes (IgG1, IgG2A, IgG2B, IgG2C and IgG3) and in rat there are four (IgG1, IgG2A, IgG2B, IgG2C).

Thus, in some embodiments of any of the aspects, the polypeptide is an antibody selected from the group consisting of IgG1 isotype, IgG isotype 2, IgG3 isotype, IgG4 isotype, IgA1 isotype, and IgA2 isotype. For example, the polypeptide is an antibody selected from the group consisting of IgG1 isotype, IgG2 isotype, IgG3 isotype and IgG4 isotype.

Methods of further modifying antibodies or antibody fragments for enhanced properties (e.g., affinity maturation, chimerization, humanization) as well as generating antigen-binding fragments, as described herein, are also well-known in the art.

In some embodiments of any of the aspects, the polypeptide comprises a detectable label and/or comprise the ability to generate a detectable signal (e.g. by catalyzing a reaction converting a compound to a detectable product).

As used herein, the term "detectable label" or "detectable marker" refers to a composition capable of producing a detectable signal. Detectable labels can comprise, for example, a light-absorbing dye, a fluorescent dye, or a radioactive label. Detectable labels, methods of detecting them, and methods of incorporating them into reagents or detection systems as described herein are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, a detection reagent is labeled with or a detection system as described herein expresses a fluorescent compound. When the fluorescently labeled reagent is exposed to light of the proper wavelength, its presence can then be detected due to fluorescence. In some embodiments of any of the aspects, a detectable label can be a fluorescent dye molecule, or fluorophore. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM™); 5-Carboxynapthofluorescein (pH 10); 5-Carboxytetramethylrhodamine (5-TAMRA™); 5-FAM™ (5-Carboxyfluorescein); 5-Hydroxy Tryptamine (HAT); 5-ROX™ (carboxy-X-rhodamine); 5-TAMRA™ (5-Carboxytetramethylrhodamine); 6-Carboxyrhodamine 6G; 6-CR 6G; 6-JOE™ (6-carboxy-4',5'-dichloro-2',7'-dimethoxyfluorescein); 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); ALEXA FLUOR® 350; ALEXA FLUOR® 430; ALEXA FLUOR® 488; ALEXA FLUOR® 532; ALEXA FLUOR® 546; ALEXA FLUOR® 568; ALEXA FLUOR® 594; ALEXA FLUOR® 633; ALEXA FLUOR® 647; ALEXA FLUOR® 660; ALEXA FLUOR® 680; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-CY7®; APTS; ASTRAZON™ Brilliant Red 4G; ASTRAZON™ Orange R; ASTRAZON™ Red 6B; ASTRAZON™ Yellow 7 GLL; Atabrine; ATTO-TAG™ CBQCA (3-(4-carboxybenzoyl) quinoline-2-carboxaldehyde); ATTO-TAG™ FQ (3-(2-furoyl) quinoline-2-carboxaldehyde); Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; BLANCOPHOR® FFG; BLANCOPHOR® SV; BOBO™-1; BOBO™-3; BODIPY® (4,4-difluoro-4-bora-3a,4a-diaza-s-indacene) BODIPY® 492/515; BODIPY® 493/503; BODIPY® 500/510; BODIPY® 505/515; BODIPY® 530/550; BODIPY® 542/563; BODIPY® 558/568; BODIPY® 564/570; BODIPY® 576/589; BODIPY® 581/591; BODIPY® 630/650-X; BODIPY® 650/665-X; BODIPY® 665/676; BODIPY® FI; BODIPY® FL ATP; BODIPY® FI-Ceramide; BODIPY® R6G SE; BODIPY® TMR; BODIPY® TMR-X conjugate; BODIPY® TMR-X, SE; BODIPY® TR; BODIPY® TR ATP; BODIPY® TR-X SE; BO-PRO™-1; BO-PRO™-3; Brilliant Sulphoflavin FF; Calcein; Calcein Blue; CALCIUM CRIMSON™; CALCIUM GREEN™; CALCIUM GREEN™-1 Ca2+ Dye; CALCIUM GREEN™-2 Ca2+; CALCIUM GREEN™-5N Ca2+; CALCIUM GREEN™-C18 Ca2+; CALCIUM ORANGE™; Calcofluor White; Carboxy-X-rhodamine (5-ROX™); CASCADE BLUER (pyrenyloxytrisulfonic acid); CASCADE YELLOW™; Catecholamine; CFDA; CFP-Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine O; Coumarin Phalloidin; CPM Methylcoumarin; CTC; CY2®; CY3.18R; CY3.5®; CY3®; CY5.1 8®; CY5.5R; CY5®; CY7R; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; DAPOXYL®; DAPOXYL® 2; DAPOXYL® 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); DIDS; Dihydorhodamine 123 (DHR); DiO (DiOC18 (3)); DiR; DiR (DiIC18 (7)); Dopamine; DSRED™ (*Discosoma* sp. red fluorescent protein); DTAF; DY-630-NHS; DY-635-NHS; EBFP; ECFP; EGFP; ELF 97™; Eosin; Erythrosin; Erythrosin ITC; Ethidium homodimer-1 (EthD-1); Euchrysin; Europium (III) chloride; Europium; EYFP; FAST BLUE™; FDA; Feulgen (Pararosaniline); FITC; FL-645; FLAZO ORANGE™; FLUO-3™; FLUO-4™: Fluorescein Diacetate; Fluoro-Emerald; FLUORO-GOLD™ (Hydroxystilbamidine); FLUORO- RUBY™. FLUORX™: FM 1-43™ (N-(3-Triethylammoniumpropyl)-4-(4-(Dibutylamino)Styryl)Pyridinium Dibromide); FM 4-46™; FURA RED™ (high pH); FURA-2™, high calcium; FURA-2™, low calcium; GENACRYL™ Brilliant Red B; GENACRYL™ Brilliant Yellow 10GF; GENACRYL™ Pink 3G; GENACRYL™ Yellow 5GF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; HOECHST® 33258 (bisbenzimide H 33258); HOECHST® 33342 (bisbenzimide H 33342); HOECHST® 34580 (bisbenzimide); HPTS; Hydroxycoumarin; Hydroxystilbamidine (FLUORO-GOLD™); Hydroxytryptamine; Indodicarbocyanine (DiD); Indotricarbocyanine (DiR); INTRAWHITE™ Cf; JC-1; JO-JO™-1; JO-PRO™-1; LASERPRO™; LAURODAN™; LDS 751™; LEUCOPHOR™ PAF; LEUCOPHOR™ SF; LEUCOPHOR™ WS; LISSAMINE™ Rhodamine; LISSAMINE™ Rhodamine B; LOLO™-1; LO-PRO™-1; Lucifer Yellow; Mag Green; Magdala Red (PHLOXIN™ B); MAGNESIUM GREEN™; MAGNESIUM ORANGE™; Malachite Green; MARINA BLUE™ (6,8-difluoro-7-hydroxy-4-methylcoumarin); MAXILON™ Brilliant Flavin 10 GFF; MAXILON™ Brilliant Flavin 8 GFF; Merocyanin; Methoxycoumarin; MITOTRACKER® Green FM; MITOTRACKER® Orange; MITOTRACKER® Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; NUCLEAR FAST™ Red; NUCLEAR™ Yellow; NYLOSAN™ Brilliant Iavin E8G; OREGON GREEN®; OREGON GREEN® 488-X; OREGON GREEN® 488 (2', 7'-difluorofluorescein); OREGON GREEN® 500; OREGON GREEN® 514; PACIFIC BLUE™ (3-carboxy-6,8-difluoro-7-hydroxycoumarin); Pararosaniline (Feulgen); PE-CY5®; PE-CY7®; PerCP; PerCP-CY5.5®; PE-TEXASRED® (Red 613); Phloxin B (Magdala Red); PHORWITE™ AR; PHORWITE™ BKL; PHORWITE™ Rev; PHORWITE™ RPA; Phosphine 3R; PHOTORESIST™; Phycoerythrin B [PE]; Phycoerythrin R [PE]; PKH26™; PKH67™; PMIA; PONTOCHROME™ Blue Black; POPO™-1; POPO™-3; PO-PRO™-1; PO-PRO™-3; Primuline; PROCION™ Yellow; Propidium Iodid (PI); PyMPO; Pyrene; Pyronine; Pyronine B; PYROZAL™ Brilliant Flavin 7GF; QSYR 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; RHODAMINE GREEN™ (carboxyrhodamine 110); Rhodamine Phallicidine; Rhodamine Phalloidine; RHODAMINE RED™; Rhodamine WT; Rose Bengal; R-phycoerythrin (PE); red shifted GFP (rsGFP, S65T); S65A; S65C; S65L; S65T; Sapphire GFP; Serotonin; SEVRON™ Brilliant Red 2B; SEVRON™ Brilliant Red 4G; SEVRON™ Brilliant Red B; SEVRON™ Orange; SEVRON™ Yellow L; SGBFP™; SGBFP™ (super glow BFP); SGGFP™; SGGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; TEXAS RED® (sulforhodamine 101 acid chloride); TEXAS RED-X® conjugate; Thiadicarbocyanine (DiSC3); Thiazine Red R; Thiazole Orange; Thioflavin 5; Thioflavin S; Thioflavin TCN; THIOLYTE™; Thiozole Orange; TINOPOL™ CBS (Calcofluor White); TMR; TO-PRO®-1; TO-PROR-3; TO-PROR-5; TOTO™-1; TOTO™-3; TriColor (PE-CY5®); TRITC (TetramethylRodamineIsoThioCyanate); TRUE BLUE™; TRURED™; ULTRALITE™; Uranine B; UVITEX™ SFC; wt GFP; WW 781; XL665; X-Rhodamine; XRITC; Xylene Orange; Y66F; Y66H; Y66W; Yellow GFP; YFP; YO-PRO™-1 (Oxazole Yellow); YO-PRO™-3 (Oxazole Red); YOYO™-1 (Oxazole Yellow Homodimer); and YOYO™-3 (Oxazole Red Homodimer). Many suitable forms of these fluorescent compounds are available and can be used. Additional fluorophore examples include, but are not limited to fluorescein, phycoerythrin, phycocyanin, o-phthalaldehyde, fluorescamine, CY3®, CY5®, allophycocyanin, TEXAS RED®, peridinin chlorophyll, cyanine, tandem conjugates such as phycoerythrin-CY5®, green fluorescent protein, rhodamine, fluorescein isothiocyanate (FITC) and OREGON GREEN®, rhodamine and derivatives (e.g., TEXAS RED® and tetramethylrhodamine isothiocyanate (TRITC)), biotin, phycoerythrin, AMCA, CYDYES®, 6-carboxyfluorescein (commonly known by the abbreviations FAM™ and F), 6-carboxy-2',4',7',4,7-hexachlorofluorescein (HEX), 6-carboxy-4',5'-dichloro-2',7'-dimethoxyfluorescein (JOE™ or J), N,N,N',N'-tetramethyl-6carboxyrhodamine (TAMRA™ or T), 6-carboxy-X-rhodamine (ROX™ or R), 5-carboxyrhodamine-6G (R6G5 or G5), 6-carboxyrhodamine-6G (R6G6 or G6), and rhodamine 110; cyanine dyes, e.g. CY3®, CY5® and CY7® dyes; coumarins, e.g., umbelliferone; benzimide dyes, e.g. HOECHST® 33258; phenanthridine dyes, e.g. TEXAS RED®; ethidium dyes; acridine dyes; carbazole dyes; phenoxazine dyes; porphyrin dyes; polymethine dyes, e.g., cyanine dyes such as CY3®, CY5®, etc.; BODIPY® (4,4-difluoro-4-bora-3a,4a-diaza-s-indacene) dyes and quinoline dyes.

Other exemplary detectable labels include luminescent and bioluminescent markers (e.g., biotin, luciferase (e.g., bacterial, firefly, click beetle and the like), luciferin, and aequorin), radiolabels (e.g., 3H, 125I, 35S, 14C, or 32P), enzymes (e.g., galactosidases, glucorinidases, phosphatases (e.g., alkaline phosphatase), peroxidases (e.g., horseradish peroxidase), and cholinesterases), and colorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference.

Means of detecting such labels are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label.

In some embodiments of any of the aspects, a detectable label can be a radiolabel including, but not limited to 3H, 125I, 35S, 14C, 32P, and 33P. Suitable non-metallic isotopes include, but are not limited to, 11C, 14C, 13N, 18F, 123I, 124I, and 125I. Suitable radioisotopes include, but are not limited to, 99mTc, 95Tc, 111In, 62Cu, 64Cu, Ga, 68Ga, and 153Gd. Suitable paramagnetic metal ions include, but are not limited to, Gd(III), Dy(III), Fe(III), and Mn(II). Suitable X-ray absorbers include, but are not limited to, Re, Sm, Ho, Lu, Pm, Y, Bi, Pd, Gd, La, Au, Au, Yb, Dy, Cu, Rh, Ag, and Ir.

In some embodiments, the radionuclide is bound to a chelating agent or chelating agent-linker attached to probe, primer or reagent. Exemplary chelating agents include, but are not limited to, diethylenetriaminepentaacetic acid (DTPA) and ethylenediaminetetraacetic acid (EDTA). Suitable radionuclides for direct conjugation include, without limitation, 3H, 18F, 124I, 125I, 131I, 35S, 14C, 32P, and 33P and mixtures thereof. Suitable radionuclides for use with a chelating agent include, without limitation, 47Sc, 64Cu, 67Cu, 89Sr, 86Y, 87Y, 90Y, 105Rh, 111Ag, 111In, 117mSn, 149Pm, 153Sm, 166Ho, 177Lu, 186Re, 188Re, 211At, 212Bi, and mixtures thereof. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to molecules such nucleic acids.

In some embodiments of any of the aspects, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments of any of the aspects, a detectable label is a chemiluminescent label, including, but not limited to lucigenin, luminol, luciferin, isoluminol, theromatic acridinium ester, imidazole, acridinium salt and oxalate ester. In some embodiments of any of the aspects, a detectable label can be a spectral colorimetric label including, but not limited to colloidal gold or colored glass or plastic (e.g., polystyrene, polypropylene, and latex) beads.

In some embodiments of any of the aspects, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromogenic substrate. Such streptavidin peroxidase detection kits are commercially available, e.g., from DAKO; Carpinteria, CA. A reagent can also be detectably labeled using fluorescence emitting metals such as 152Eu, or others of the lanthanide series. These metals can be attached to the reagent using such metal chelating groups as diethylenetriaminepentaacetic acid (DTPA) or ethylenediaminetetraacetic acid (EDTA).

Labeled polypeptides described herein can be used, for example, diagnostically and/or experimentally in a number of contexts, including (i) to isolate histamine by standard techniques, such as affinity chromatography or immunoprecipitation; (ii) to detect histamine; (iii) to monitor histamine levels in tissue as part of a clinical testing procedure, e.g., to determine the efficacy of a given anti-histamine treatment regimen.

In some embodiments of any of the aspects, the polypeptide comprises a therapeutic agent. For example, a therapeutic agent is linked, covalently or non-covalently to the polypeptide.

Non-limiting Examples of therapeutic agents include Brompheniramine (DIMETANE®), Cetirizine (ZYRTEC®), Chlorpheniramine (CHLOR-TRIMETON®), Clemastine (TAVIST®), Diphenhydramine (BENADRYL®), Fexofenadine (ALLEGRA®), Loratadine (ALAVERT®, CLARITIN®), loperamide, atropine, and bismuth subsalicylate.

In some embodiments of the various aspects, a polypeptide describe herein has a dissociation constant ($K_D$) for binding with histamine of $1\times10^{-6}$ M or less; $5\times10^{7}$ M or less; $1\times10^{-7}$ M or less; $5\times10^{-8}$ M or less; $1\times10^{-8}$ M or less; $5\times10^{-9}$ M or less; or $1\times10^{-9}$ M or less. In one embodiment, a polypeptide described herein has a $K_D$ from $1\times10^{-7}$ M to $1\times10^{-10}$M. In one embodiment, a polypeptide described herein has a $K_D$ from $1\times10^{-8}$ M to $1\times10^{-10}$ K M. In one embodiment, the affinity is determined using Octet methods.

Those of ordinary skill in the art will appreciate standard methods known for determining the $K_D$. For example, in one embodiment, $K_D$ is measured by a radiolabeled antigen binding assay (RIA). In one embodiment, an RIA is performed with the Fab version of the polypeptide and its antigen, e.g., histamine and/or histidine. For example, solution binding affinity of the polypeptide is measured by equilibrating the Fab form of the polypeptide with a minimal concentration of ($^{125}$I)-labeled histamine in the presence of a titration series of unlabeled histamine, then capturing bound histamine with an anti-Fab antibody-coated plate (see, e.g., Chen et al., J. Mol. Biol. 293:865-881(1999)). According to another embodiment, $K_D$ is measured using a BIACORE surface plasmon resonance assay. The term "surface plasmon resonance", as used herein, refers to an optical phenomenon that allows for the analysis of real-time interactions by detection of alterations in protein concentrations within a biosensor matrix, for example using the BIACORE system (Biacore Life Sciences division of GE Healthcare, Piscataway, NJ).

Figure 1A:
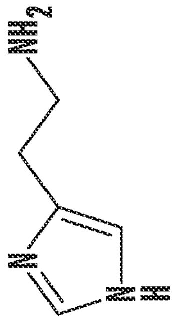
FIG. 1A shows the structure of a histamine molecule.

In some embodiments, the polypeptides bind to free histamine and/or histidine with high affinity, e.g., with a $K_D$ that is at least about 10%, 20%, 30%, 40%, 50%, 60%, 70%, 80% or 90% lower than the $K_D$ of an anti-histamine and/or histidine antibody molecule that was raised by conjugating histamine to a large immunogenic protein carrier, such as bovine serum albumin (BSA) or ovalbumin (OVA) via its primary amine group (see, FIGS. 1A-1B).

In some embodiments, the polypeptides, antibodies and/or antibody fragments engineered for enhanced binding to free histamine and/or histidine has improved stability, e.g., at least about 0.5, 1, 2, 3, 4, 5, 6, 7, 8, 9 or 10-fold more stable in vivo or in vitro, than an anti-histamine and/or histidine antibody molecule that was raised by conjugating histamine to a large immunogenic protein carrier, such as bovine serum albumin (BSA) or ovalbumin (OVA) via its primary amine group (see, FIGS. 1A-1B).

In some embodiments of any of the aspects, the VL domain comprises an amino acid sequence having at least 85%, 86%, 87%, 88%, 89%, 90%, 91%, 92%, 93%, 94%, 95%, 96%, 97%, 98% or 99% identity to sequence: the amino acid DVLMTQTPLSLPVSLGDQASFSCRSSQSIVHSNGNTYLEWYLQKPGQSPKLLIYKVSNRF SGVPDRFSGSGSGTDFTLKISRVEAEDLGVYYCFQASHVPYTFGGGTKLELKRA (SEQ ID NO: 78). For example, the VL domain comprises an amino acid sequence having at least 90%, 91%, 92%, 93%, 94%, 95%, 96%, 97%, 98% or 99% identity to SEQ ID NO: 78. In some embodiments of the various aspects described herein, the VL domain comprises an amino acid sequence having at 97%, 98% or 99% identity to SEQ ID NO: 78. In some embodiments of the various aspects described herein, the VL domain comprises an amino acid sequence having 100% identity to SEQ ID NO: 78.

In some embodiments of any of the aspects, the VH domain comprises an amino acid sequence having at least 85%, 86%, 87%, 88%, 89%, 90%, 91%, 92%, 93%, 94%, 95%, 96%, 97%, 98% or 99% identity to the amino acid sequence: EVQLQQSGGELVKPGASVKISCK-ASGYSFTGYNMNWVKQTHGKSLEWIGNINPYYGST RYNQKFKGKATLTVDKSSSTAYMQLNSLTYED-SAVYYCARDDDYGEIDYFDYWGQGT TITVYS (SEQ ID NO: 79). For example, the VH domain comprises an amino acid sequence having at least 90%, 91%, 92%, 93%, 94%, 95%, 96%, 97%, 98% or 99% identity to SEQ ID NO: 79. In some embodiments of the various aspects described herein, the VH domain comprises an amino acid sequence having at 97%, 98% or 99% identity to SEQ ID NO: 79. In some embodiments of the various aspects described herein, the VH domain comprises an amino acid sequence having 100% identity to SEQ ID NO: 79.

In some embodiments of any of the aspects, the polypeptide comprises an amino acid sequence having at least 85%, 86%, 87%, 88%, 89%, 90%, 91%, 92%, 93%, 94%, 95%, 96%, 97%, 98% or 99% identity to the amino acid sequence:

```
                                         (SEQ ID NO: 80)
DVLMTQTPLSLPVSLGDQASFSCRSSQSIVHSNGNTYLEWYLQKPGQSP

KLLIYKVSNRFSGVPDRFSGSGSGTDFTLKISRVEAEDLGVYYCFQASH

VPYTFGGGTKLELKRAEGKSSGSGSESKASEVQLQQSGGELVKPGASVK

ISCKASGYSFTGYNMNWVKQTHGKSLEWIGNINPYYGSTRYNQKFKGKA

TLTVDKSSSTAYMQLNSLTYEDSAVYYCARDDDYGEIDYFDYWGQGTTI

TVYS.
```

For example, the polypeptide comprises an amino acid sequence having at least 90%, 91%, 92%, 93%, 94%, 95%, 96%, 97%, 98% or 99% identity to SEQ ID NO: 80. In some embodiments of the various aspects described herein, the For example, the VH domain comprises an amino acid sequence having at least 90%, 91%, 92%, 93%, 94%, 95%, 96%, 97%, 98% or 99% identity to SEQ ID NO: 80. In some embodiments of the various aspects described herein, the polypeptide comprises an amino acid sequence having at 97%, 98% or 99% identity to SEQ ID NO: 80. In some embodiments of the various aspects described herein, the polypeptide comprises an amino acid sequence having 100% identity to SEQ ID NO: 80.

The disclosure also provides a polynucleotide encoding a polypeptide described herein. The skilled person will understand that, due to the degeneracy of the genetic code, a given polypeptide can be encoded by different polynucleotides. These "variants" are encompassed herein.

In some embodiments, a nucleic acid encoding a polypeptide described herein is comprised in a vector. In some embodiments, a nucleic acid sequence encoding a Fc fusion protein described herein, or any part thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments, the expression system is an organism other than the source of the native/wild-type sequence (or a cell obtained from such organism). In some embodiments, the vector and/or nucleic acid sequence described herein is codon-optimized for expression in a mammal or mammalian cell, e.g., a mouse, a murine cell, or a human cell. In some embodiments, the vector and/or nucleic acid sequence described herein is codon-optimized for expression in a human cell. In some embodiments, the vector and/or nucleic acid sequence described herein is codon-optimized for expression in a yeast or yeast cell. In some embodiments, the vector and/or nucleic acid sequence described herein is codon-optimized for expression in a bacterial cell. In some embodiments, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments of any of the aspects described herein, the constructs can be comprised by a superstructure, e.g., nanoparticles, liposomes, vectors, cells, scaffolds, or the like.

The disclosure also provides a host cell comprising a polynucleotide described herein or a plasmid or vector described herein. As used herein, the term "cell" refers to a single cell as well as to a population of (i.e., more than one) cells. A host cell can be a prokaryotic or eukaryotic host cell. Exemplary host cells include, but are not limited to, bacterial cells, yeast cells, plant cell, animal (including insect) or human cells.

The host cells can be employed in a method of producing a polypeptide described herein. Generally, the method comprises: culturing a host cell comprising a polynucleotide described herein or a plasmid or vector described herein under conditions such that the Fc fusion protein is expressed; and optionally recovering the polypeptide from the culture medium. The polypeptide can be concentrated and purified by a variety of biochemical and chromatographic methods, including methods utilizing differences in size, charge, hydrophobicity, solubility, specific affinity, etc. between the polypeptide and other substances in the cell culture medium. In some embodiments, the polypeptide is secreted from the host cells.

The polypeptide described herein can be produced as recombinant molecules in prokaryotic or eukaryotic host cells, such as bacteria, yeast, plant, animal (including insect) or human cell lines or in transgenic animals. Recombinant methods of producing a polypeptide through the introduction of a vector including nucleic acid encoding the polypeptide into a suitable host cell is well known in the art, such as is described in Sambrook et al., Molecular Cloning: A Laboratory Manual, 2d Ed, Vols 1 to 8, Cold Spring Harbor, NY (1989); M. W. Pennington and B. M. Dunn, Methods in Molecular Biology: Peptide Synthesis Protocols, Vol 35, Humana Press, Totawa, NJ (1994), contents of both of which are herein incorporated by reference.

The production of polypeptide at high levels in suitable host cells requires the assembly of the polynucleotides encoding such Fc fusion proteins into efficient transcriptional units together with suitable regulatory elements in a recombinant expression vector that can be propagated in various expression systems according to methods known to those skilled in the art. Efficient transcriptional regulatory elements could be derived from viruses having animal cells as their natural hosts or from the chromosomal DNA of animal cells. For example, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA, the transcriptional unit should contain in its 3'-proximal part a DNA region encoding a transcriptional termination-polyadenylation sequence. Generally, this sequence can be derived from the Simian Virus 40 early transcriptional region, the rabbit beta-globin gene, or the human tissue plasminogen activator gene.

The vector is transfected into a suitable host cell line for expression of the polypeptide. Examples of cell lines that can be used to prepare the polypeptide described herein include, but are not limited to monkey COS-cells, mouse L-cells, mouse C127-cells, hamster BHK-21 cells, human embryonic kidney 293 cells, and hamster CHO-cells.

The expression vector encoding the polypeptide can be introduced in several different ways. For instance, the expression vectors can be created from vectors based on different animal viruses. Examples of these are vectors based on baculovirus, vaccinia virus, adenovirus, and preferably bovine papilloma virus The transcription units encoding the corresponding DNAs can also be introduced into animal cells together with another recombinant gene, which may function as a dominant selectable marker in these cells in order to facilitate the isolation of specific cell clones, which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated to the genome of the host cell, frequently resulting in a tight physical linkage between the different transcription units Other types of selectable marker genes, which can be used together with the cDNA of the desired protein are based on various transcription units encoding dihydrofolate reductase (dhfr). After introduction of this type of gene into cells lacking endogenous dhfr-activity, preferentially CHO-cells (DUKX-B11, DG-44) it will enable these to grow in media lacking nucleosides. An example of such a medium is Ham's F12 without hypoxanthine, thymidin, and glycine. These dhfr-genes can be introduced together with the Kazal-type serine protease inhibitors' cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at a very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a batch culture or as a perfusion culture with continuous production of conditioned medium over extended periods of time. Thus, according to the present invention, the above cell lines are well suited for the development of an industrial process for the production of the desired recombinant proteins.

Exemplary genera of yeast contemplated to be useful in the production of the Fc fusion protein described herein as hosts are *Pichia* (formerly classified as *Hansenula*), *Saccharomyces, Kluyveromyces, Aspergillus, Candida, Torulopsis, Torulaspora, Schizosaccharomyces, Citeromyces, Pachysolen, Zygosaccharomyces, Debaromyces, Trichoderma, Cephalosporium, Humicola, Mucor, Neurospora, Yarrowia, Metschunikowia, Rhodosporidium, Leucosporidium, Botryoascus, Sporidiobolus, Endomycopsis*, and the like. Genera include those selected from the group consisting of *Saccharomyces, Schizosaccharomyces, Kluyveromyces, Pichia* and *Torulaspora*. Examples of *Saccharomyces* spp. are *S. cerevisiae, S. italicus* and *S. rouxii.*

Suitable promoters for *S. cerevisiae* include those associated with the PGKI gene, GAL1 or GAL10 genes, CYCI, PHO5, TRPI, ADH1, ADH2, the genes for glyceral-dehyde-3-phosphate dehydrogenase, hexokinase, pyruvate decarboxylase, phos-phofructokinase, triose phosphate isomerase, phosphoglucose isomerase, glucokinase, alpha-mating factor pheromone, the PRBI, the GUT2, the GPDI promoter, and hybrid promoters involving hybrids of parts of 5' regulatory regions with parts of 5' regulatory regions of other promoters or with upstream activation sites (e.g. the promoter of EP-A-258 067).

Convenient regulatable promoters for use in *Schizosaccharomyces pombe* are the thiamine-repressible promoter from the nmt gene as described by Maundrell (Maundrell K. 1990. Nmt1 of fission yeast. A highly transcribed gene completely repressed by thiamine. J. Biol. Chem. 265: 10857-10864) and the glucose repressible jbpl gene promoter as described by Hoffman and Winston (Hoffman C S and Winston F. 1990. Isolation and characterization of mutants constitutive for expression of the fbp1 gene of *Schizosaccharomyces pombe*. Genetics 124:807-816).

The transcription termination signal may be the 3' flanking sequence of a eukaryotic gene which contains proper signals for transcription termination and polyadenylation. Suitable 3' flanking sequences may, for example, be those of the gene naturally linked to the expression control sequence used, i.e. may correspond to the promoter. Alternatively, they may be different in which case the termination signal of the *S. cerevisiae* ADHI gene is optionally used.

Exemplary expression systems for the production of the Fc fusion protein described herein in bacteria include *Bacillus subtilis, Bacillus brevis, Bacillus megaterium, Caulobacter crescentus*, and, most importantly, *Escherichia coli* BL21 and *E. coli* K12 and their derivatives. Convenient promoters include but are not limited to trc promoter, tac promoter, lac promoter, lambda phage promoter $p_L$, the L-arabinose inducible araBAD promoter, the L-rhamnose inducible rhaP promoter, and the anhydrotetracycline-inducible tetA promoter/operator.

In some embodiment, a polynucleotide encoding the polypeptide described herein can be fused to signal sequences which will direct the localization of a polypeptide described herein to particular compartments of a prokaryotic cell and/or direct the secretion from a prokaryotic cell. For example, in *E. coli*, one may wish to direct the expression of the polypeptide to the periplasmic space. Examples of signal sequences or proteins (or fragments thereof) to which the polypeptides described herein may be fused in order to direct the expression of the polypeptide to the periplasmic space of bacteria include, but are not limited to, the pelB signal sequence, the maltose binding protein signal sequence, the ompA signal sequence, the signal sequence of the periplasmic *E. coli* heat-labile enterotoxin B-subunit, and the signal sequence of alkaline phosphatase. Several vectors are commercially available for the construction of fusion proteins which will direct the localization of a protein, such as the pMAL series of vectors (NEW ENGLAND BIOLABS).

Exemplary plant systems for expression of the polypeptide described herein include tobacco, potato, rice, maize, soybean, alfalfa, tomato, lettuce and legume (summarized by Ma J K C et al. 2003. The production of recombinant pharmaceutical proteins in plants. Nat. Rev. Genet. 4:794-805). Expression of recombinant proteins in plant systems may be directed by suitable regulatory elements to specific organs or tissues such as fruits, seeds, leaves or tubers. Alternatively, proteins may be secreted from the roots. Within the cell, proteins may be targeted to particular compartments, e.g. the endoplasmic reticulum, protein bodies or plastids. There the product may accumulate to higher levels or undergo particular forms of posttranslational modification.

Exemplary examples for large-scale transgenic expression systems (for review see Pollock D P. 1999. Transgenic milk as a method for the production of recombinant antibodies. J Immunol Methods 231:147-157) include rabbit (Chrenek P et al. 2007. Expression of recombinant human factor VIII in milk of several generations of transgenic rabbits. Transgenic Res. 2007 Jan. 31), goat (Lazaris A et al. 2006. Transgenesis using nuclear transfer in goats. Methods Mol Biol. 348:213-26), pig and cattle.

In another aspect, the disclosure provides a composition comprising a polypeptide or polynucletide described herein. In some embodiments, the composition further comprises a pharmaceutically acceptable excipient or carrier. Pharmaceutically acceptable carriers and diluents include saline, aqueous buffer solutions, solvents and/or dispersion media. Acceptable formulation materials preferably are nontoxic to recipients at the dosages and concentrations employed. In some embodiments, the formulation material(s) are selected based on their suitability for subcutaneous and/or I.V. administration. The formulation materials can be selected based on their ability to modify, maintain or preserve, for example, the pH, osmolality, viscosity, clarity, color, isotonicity, odor, sterility, stability, rate of dissolution or release, adsorption, penetration, or any combination thereof, of the pharmaceutical composition. The use of such carriers and diluents is well known in the art. Some non-limiting examples of materials which can serve as pharmaceutically-acceptable carriers include: sugars, such as lactose, glucose, sucrose, mannose, and dextrins; starches, such as corn starch and potato starch; cellulose, and its derivatives, such as sodium carboxymethyl cellulose, methylcellulose, ethyl cellulose, microcrystalline cellulose and cellulose acetate; powdered tragacanth; malt; gelatin; lubricating agents, such as magnesium stearate, sodium lauryl sulfate and talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol (PEG); esters, such as ethyl oleate and ethyl laurate; agar; buffers and buffering agents, such as borate, bicarbonate, Tris-HCl, citrates, phosphates, other organic acids magnesium hydroxide, and aluminum hydroxide; alginic acid; pyrogen-free water; isotonic saline; Ringer's solution; ethyl alcohol; pH buffered solutions; polyesters, polycarbonates and/or polyanhydrides; bulking agents, such as polypeptides and amino acids (such as glycine, glutamine, asparagine, arginine or lysine); serum components, such as serum albumin, HDL, and LDL; $C_2$-$C_{12}$ alcohols, such as ethanol; antimicrobials; antioxidants (such as ascorbic acid, sodium sulfite or sodium hydrogen-sulfite); chelating agents (such as ethylenediamine tetraacetic acid (EDTA)); complexing agents (such as caffeine, polyvinylpyrrolidone, beta-cyclodextrin or hydroxypropyl-beta-cyclodextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients; pharmaceutical adjuvants; and/or other non-toxic compatible substances employed in pharmaceutical formulations. See, for example, Allen (2012) *Remington—The Science and Practice of Pharmacy,* 22d Edition, Lloyd V, Allen, ed., The Pharmaceutical Press. Wetting agents, coloring agents, release agents, coating agents, sweetening agents, flavoring agents, perfuming agents, preservative and antioxidants can also be present in the formulation. The terms such as "excipient," "carrier", "pharmaceutically acceptable carrier" or the like are used interchangeably herein. In some embodiments, the carrier inhibits the degradation of the active agent, e.g., a combination, construct, unit, or composition as described herein. In certain embodiments, the optimal pharmaceutical composition is determined by one skilled in the art depending upon, for example, the intended route of administration, delivery format and desired dosage. See, for example, Allen (2012) *Remington—The Science and Practice of Pharmacy,* 22d Edition, Lloyd V, Allen, ed., The Pharmaceutical Press.

In some embodiments, the pharmaceutical composition described herein can be in a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

In some embodiments, the formulation components are present in concentrations that are acceptable to the site of administration. In some embodiments, buffers are used to maintain the composition at physiological pH or at a slightly lower pH, typically within a pH range of from about 5 to about 8.

Suitable vehicles that can be used to provide parenteral dosage forms of the compositions described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an agent as disclosed herein can also be incorporated into the parenteral dosage forms of the disclosure, including conventional and controlled-release parenteral dosage forms.

It is recognized that biologics, such as antibodies or other protein-based constructs, are not generally suitable for oral administration. However, depending upon the receptor(s) one wishes to target, oral formulations for delivery to the gut via, e.g., enteric coatings or encapsulation are specifically contemplated. In some embodiments of any of the aspects, the composition provided is formulated for self-administration.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the pharmaceutical composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (ALZA CORPORATION, Mountain View, Calif. USA)), or a combination thereof to provide the desired release profile in varying proportions.

The pharmaceutical composition to be used for in vivo administration typically is sterile. In certain embodiments, sterilization is accomplished by filtration through sterile filtration membranes. In those embodiments where the pharmaceutical composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In some embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In some embodiments of any of the aspects, the composition provided is formulated for self-administration.

In another aspect, the disclosure provides a cell comprising a polypeptide described herein or a polynucleotide encoding same. For example, a cell prokaryotic cell or a eukaryotic cell comprising a polypeptide or polynucleotide described herein.

In yet another aspect, the disclosure provide a kit comprising a polypeptide described herein or a polynucleotide encoding same.

A variety of kits and components can be prepared for use in the methods described herein, depending upon the intended use of the kit. Accordingly, in another aspect, provided herein is a kit comprising a polypeptide described herein or a nucleic acid encoding a polypeptide described herein. A kit is any manufacture (e.g., a package or container) comprising a polypeptide or a polynucleotide encoding a polypeptide described herein. The manufacture can be promoted, distributed, or sold as a unit for performing the methods described herein.

The kits described herein can optionally comprise additional components and reagents. As will be appreciated by one of skill in the art, components of the kit can be provided in any desired form, e.g., in a lyophilized form, a liquid form, a solid form, or a concentrated. In some embodiments of the various aspects described herein, the kit can comprise ampoules, syringes, or the like.

In some embodiments, the kit can comprise informational material. The informational material can be descriptive, instructional, marketing or other material that relates to the methods described herein. The informational material of the kits is not limited in its form. In some embodiments, the informational material can include information about production of the reagents, concentration, date of expiration, batch or production site information, and so forth. In one embodiment, the informational material relates to methods for using or administering the components of the kit.

It is notes that the components of a kit can provided singularly or in any combination as a kit. Such a kit includes the components described herein and packaging materials thereof.

In some embodiments, the compositions in a kit can be provided in a watertight or gas tight container which in some embodiments is substantially free of other components of the kit. For example, the reagents described herein can be supplied in more than one container, e.g., it can be supplied in a container having sufficient reagent for a predetermined number of applications, e.g., 1, 2, 3 or greater. One or more components as described herein can be provided in any form, e.g., liquid, dried or lyophilized form. Liquids or components for suspension or solution of the reagents can be provided in sterile form and should not contain microorganisms or other contaminants. When the components described herein are provided in a liquid solution, the liquid solution preferably is an aqueous solution.

The kit will typically be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time.

In some embodiments of any of the aspects, the polypeptide or a kit or composition comprising the same can be used for detection of histamine, medical diagnostics, early detection of diseases and/or for food safety applications.

In some embodiments of any of the aspects, the kit or composition described herein can comprise histamine inhibitors e.g. copper-chelating agents, eg cyanide Carbonylgroup reagents, including but not limited to aminoguanidine and semibarbacide.

In some embodiments of any of the aspects, the kit or composition can further comprise a therapeutic agent. For example, an anti-allergic and/or an anti-diarrhea agent.

In another aspect, the disclosure provides an analyte detection system comprising a polypeptide described herein. It is noted that the analyte detection system can be based on spectroscopic, photochemical, biochemical, immunochemical, electrical, optical or chemical detection or any combinations thereof.

In some embodiments of any of the aspects, the detection system comprises an enzyme-linked immunosorbent assay (ELISA), fluorescent linked immunosorbent assay (FLISA), immunofluorescent microscopy, fluorescence in situ hybridization (FISH), magnetic and/or electrochemical detection, or any other radiological, chemical, enzymatic or optical detection assay and/or any other assay described herein or known in the art.

In some embodiments of any of the aspects, said detection system comprises a lateral flow assay (LFA). Lateral flow tests operate on the same principles as the enzyme-linked immunosorbent assays. In essence, these tests run the liquid sample along the surface of a pad with reactive molecules that show a visual positive or negative result. The pads are based on a series of capillary beds, such as pieces of porous paper-microstructured polymer, or sintered polymer. Each of these pads has the capacity to transport fluid (e.g., urine, blood, saliva) spontaneously. Exemplary LFA assays include sandwich assays, competitive assays. Lateral flow assays can test a variety of samples like urine, blood, saliva, sweat, serum, and other fluids.

The disclosure also provides a use of a polypeptide described herein for detecting histamine and/or histidine. The assay for detecting histamine and/or histadine can be based on spectroscopic, photochemical, biochemical, immunochemical, electrical, optical or chemical detection or any combinations thereof. For example, an assay for detecting histamine and/or histadine using a polypeptide described herein can be an enzyme-linked immunosorbent assay (ELISA), fluorescent linked immunosorbent assay (FLISA), immunofluorescent microscopy, fluorescence in situ hybridization (FISH), magnetic and/or electrochemical detection, or any other radiological, chemical, enzymatic or optical detection assay and/or any other assay described herein or known in the art.

In some embodiments of any of the aspects, the assay for detecting histamine and/or histadine using a polypetide described herein comprises a lateral flow assay (LFA).

Methods of Treatment

The polypeptides and polynucleotides described herein can be useful for the treatment of diseases and/or conditions caused or involving a histamine imbalance, including, but not limited to histapenia, histadelia and/or an allergy.

Thus, in some aspects, the methods relate to treating a subject having or diagnosed as having a diseases and/or conditions caused or involving a histamine imbalance, including, but not limited to histapenia, histadelia and/or an allergy.

Also provided herein, in some aspects, are methods of delaying or reducing the intensity of a relapse or flare of a diseases and/or conditions caused or involving a histamine imbalance, including, but not limited to histapenia, histadelia and/or an allergy, comprising administering to the subject an effective amount of polynucleotides, polypeptides, antibodies and/or antibody fragments engineered for enhanced binding to free histamine and/or histidine described herein. The second therapy can be administered to the subject before, concurrently with, or after administration of an effective amount of polynucleotides, polypeptides, antibodies and/or antibody fragments engineered for enhanced binding to free histamine and/or histidine described herein.

As used herein, a "diseases and/or conditions caused or involving a histamine imbalance" is characterized by the inability of one's body to maintain a basal plasma histamine concentration of ~0.3-1.0 ng/ml. Exceeding the individual histamine tolerance gives rise to concentration-dependent histamine-mediated symptoms. For example, abnormally high histamine levels can lead to excessive allergies (or hyperactive responses to allergens), hyperactivity, compulsive or obsessive behavior, vertigo, inner ear pressure, depression, anxiety, panic attacks, migraine headaches, heightened emotional sensitivity and/or suicidal tendencies. Reduced histamine levels can lead to depressed metabolism and/or weight gain, paranoia, grandiosity, hallucinations (e.g., classic schizophrenic symptoms), tinnitus, hirsutism, visual and auditory abnormalities, anxiety and food sensitivities.

In some embodiments, any of the methods of treating a subject having or diagnosed as having a diseases and/or condition caused or involving a histamine imbalance or reducing the intensity of a relapse or flare further comprise administering a second therapy to the subject.

In some aspects and embodiments of the methods described herein, administration of the polynucleotides, polypeptides, antibodies and/or antibody fragments engineered for enhanced binding to free histamine and/or histidine decreases the symptoms of histapenia, histadelia and/or an allergic reaction.

Thus, in some aspects, the invention provides the use of a polypeptide described herein in a method of treatment.

The compositions (e.g., combination and/or constructs) described herein can be administered to a subject having or diagnosed as having diseases and/or conditions caused or involving a histamine imbalance in order to treat their condition. Treating or treatment of any disease or condition refers to ameliorating a disease or condition that exists in a subject. In some embodiments, the methods described herein comprise administering an effective amount of compositions described herein to a subject in order to alleviate one or more symptoms of a diseases and/or conditions caused or involving a histamine imbalance or condition. As used herein, "alleviating a symptom" is ameliorating any condition or symptom associated with the disease or condition. As compared with an equivalent untreated control, such reduction is by at least 5%, at least 10%, at least 20%, at least 30%, at least 40%, at least 50%, at least 60%, at least 70%, at least 80%, at least 90%, at least 95%, at least 99% or more as measured by any standard technique. Thus, treating or treatment includes ameliorating at least one physical parameter or symptom. Treating or treatment includes modulating the disease or condition, either physically (e.g., stabilization of a discernible symptom) or physiologically (e.g., stabilization of a physical parameter) or both, as well as delaying or preventing progression of an autoimmune condition. For example, a method for treating diseases and/or condition caused or involving a histamine imbalance is considered to be a treatment if there is a 10% reduction in one or more symptoms of the histamine imbalance condition (for example, excessive allergies (or hyperactive responses to allergens), hyperactivity, compulsive or obsessive behavior, vertigo, inner ear pressure, depression, anxiety, panic attacks, migraine headaches, heightened emotional sensitivity and/or suicidal tendencies. Reduced histamine levels can lead to depressed metabolism and/or weight gain, paranoia, grandiosity, hallucinations (e.g., classic schizophrenic symptoms), tinnitus, hirsutism, visual and auditory abnormalities, anxiety and food sensitivities, etc.) in a subject as compared to a control. It is understood that treatment does not necessarily refer to a cure or complete ablation of the disease, condition, or symptoms of the disease or condition.

Subjects having diseases and/or condition caused or involving a histamine imbalance, e.g. histapenia, histadelia and/or an allergy can be identified by a physician using current methods of diagnosing the disease.

A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or injectable administration. Administration can be local or systemic.

The term "effective amount" as used herein refers to the amount of a combination and/or construct as described herein needed to alleviate at least one or more symptom of the disease or disorder, and relates to a sufficient amount of pharmacological composition to provide the desired effect. The term "therapeutically effective amount" therefore refers to an amount of a combination and/or construct as described herein that is sufficient to provide a particular anti-allergenic effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

A suitable dose of a construct or antibody or fragment thereof described herein capable of treating diseases and/or condition caused or involving a histamine imbalance, e.g. histapenia, histadelia and/or an allergy in a subject, can depend on a variety of factors including the particular construct used and whether it is used concomitantly with other therapeutic agents. For example, a different dose of a whole antibody may be required to treat a subject with an autoimmune disorder as compared to the dose of an antigen-binding portion of the same antibody (e.g., Fab' antibody fragment) required to treat the same subject. Other factors affecting the dose administered to the subject include, e.g., the type or severity of the autoimmune disorder. For example, a subject having histadelia may require administration of a different dosage than a subject with an allergy. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject also depends upon the judgment of the treating medical practitioner. A therapeutically effective amount is also one in which any toxic or detrimental effects of the composition are outweighed by the therapeutically beneficial effects.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a combination and/or construct as described herein which achieves a half-maximal inhibition of symptoms) as determined in cell culture, or in an appropriate animal model. Levels in plasma can be measured, for example, by high performance liquid chromatography. The dosage can be determined by a physician and adjusted, as necessary, to suit observed effects of the treatment.

In some embodiments of any of the methods described herein, the construct or antibody or antigen-binding portion thereof as described herein is administered as a monotherapy, e.g., another treatment for the diseases and/or condition caused or involving a histamine imbalance, e.g. histapenia, histadelia and/or an allergy is not administered to the subject.

In some embodiments, the methods described herein can further comprise having previously administered, co-administering, or administering a second agent and/or treatment to the subject, e.g. as part of a combinatorial therapy. In some embodiments of any of the aspects, the subject can have previously been administered, is co-administered, or administered a further anti-allergenic agent.

In some embodiments of any of the aspects, an effective dose of a composition comprising a combination and/or construct as described herein can be administered to a patient once. In certain embodiments, an effective dose of a composition comprising a combination and/or construct as described herein can be administered to a patient repeatedly. For systemic administration, subjects can be administered a therapeutic amount of a composition comprising a combination and/or construct such as, e.g., 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. T cell activity and/or proliferation by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient(s). The desired dose or amount of activation can be administered at one time or divided into sub-doses, e.g., 2-4 sub-doses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising a combination and/or construct as described herein can be administered over a period of time, such as over a 5 minute, 10 minute, 15 minute, 20 minute, or 25 minute period.

The dosage ranges for the administration of a construct or antibody or antigen-binding portion thereof as described herein, according to the methods described herein depend upon, for example, the form of the composition, its potency, and the extent to which symptoms, markers, or indicators of a condition described herein are desired to be reduced, for example the percentage reduction desired for, e.g., T cell activation or proliferation or cytokine production. The dosage should not be so large as to cause adverse side effects, such as T cell exhaustion. Generally, the dosage will vary with the age, condition, and sex of the patient and can be determined by one of skill in the art. The dosage can also be adjusted by the individual physician in the event of any complication.

The efficacy of a combination and/or construct as described herein in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of a mouse model of an autoimmune disease. When using an experimental animal model, efficacy of treatment is evidenced when a statistically significant change in a marker is observed.

In vitro and animal model assays are provided herein that allow the assessment of a given dose of a combination or construct as described herein. By way of non-limiting example, the effects of a dose of a combination or construction as described herein can be assessed by measuring the activity and/or proliferation of activated cultured cells.

Some exemplary embodiments of the disclosure can be described by the following numbered embodiments:

Embodiment 1: A polypeptide comprising: (a) a variable heavy chain (VH) domain comprising: (i) a complementarity determining region 1 (VH CDR1) comprising an amino acid sequence having at least 85% identity to an amino acid sequence selected from the group consisting of: AVALGGNMN (SEQ ID NO: 1) and YSFTGYNMN (SEQ ID NO: 2), (ii) a complementarity determining region 2 (VH CDR2) comprising an amino acid sequence having at least 85% identity to an amino acid sequence selected from the group consisting of: WIGNIAVAIGLTRY (SEQ ID NO: 3) and WIGNINPYYGSTRY (SEQ ID NO: 4), and (iii) a complementarity determining region 3 (VH CDR3) comprising an amino acid sequence having at least 85% identity to the amino acid sequence selected from the group consisting of: RDDDYGEIDYFDY (SEQ ID NO: 5) and RAGVKGNILAAGN (SEQ ID NO: 83); and (b) a variable light chain (VL) domain comprising: (i) a complementarity determining region 1 (VL CDR1) comprising an amino acid sequence having at least 85% identity to an amino acid sequence selected from the group consisting of:

```
                              (SEQ ID NO: 6)
QSIVHSNGNTYLE,

                              (SEQ ID NO: 7)
QSLVHSGGNTYLE,

                              (SEQ ID NO: 8)
QSIVHSSGNTYLE,

                              (SEQ ID NO: 9)
QSLVHSSGNTYLE,
```

-continued

```
                              (SEQ ID NO: 10)
QSIVHSGGNTYLE,

                              (SEQ ID NO: 11)
QTIVHSNGNTYLE,

                              (SEQ ID NO: 12)
QSIVHSDGNTYLE,

                              (SEQ ID NO: 13)
QSIVSSSGNTYLE,

                              (SEQ ID NO: 14)
QSIVYSDGNTYLE,

                              (SEQ ID NO: 15)
QTIVHSSGNTYLE,

                              (SEQ ID NO: 16)
QSIVHRDGNTYLE,

                              (SEQ ID NO: 17)
QSLVHSDGNTYLE,

                              (SEQ ID NO: 18)
QTIVHSNGNTYLE,

                              (SEQ ID NO: 19)
GVAGANAGAGALA, and

                              (SEQ ID NO: 20)
QSIVYSSGNTYLE,
```

(ii) a complementarity determining region 1 (VL CDR2) comprising an amino acid sequence having at least 85% identity to an amino acid sequence selected from the group consisting of: LLIYAVKATGA (SEQ ID NO: 21), LLIYKVSNRFS (SEQ ID NO: 22); and (iii) a complementarity determining region 1 (VL CDR3) comprising an amino acid sequence selected from the group consisting of: SQATHVPY (SEQ ID NO: 23), AGAVAVAA (SEQ ID NO: 24) and FQASHVPY (SEQ ID NO: 25).

Embodiment 2: The polypeptide of Embodiment 1, wherein the VL CDR1 comprises an amino acid sequence having at least 85% identity to the amino acid sequence QSIVHSNGNTYLE (SEQ ID NO: 6), the VL CDR2 comprises an amino acid sequence having at least 85% identity to the amino acid sequence LLIYKVSNRFS (SEQ ID NO: 22), and the VL CDR3 comprises an amino acid sequence having at least 85% identity to the amino acid sequence FQASHVPY (SEQ ID NO: 25).

Embodiment 3: The polypeptide of any one of Embodiments 1-2, wherein the VH CDR1 comprises an amino acid sequence having at least 85% identity to the amino acid sequence YSFTGYNMN (SEQ ID NO: 2), the VH CDR2 comprises an amino acid sequence having at least 85% identity to the amino acid sequence WIGNINPYYGSTRY (SEQ ID NO: 4), and the VH CDR3 comprises an amino acid sequence having at least 85% identity to the amino acid sequence RDDDYGEIDYFDY (SEQ ID NO: 5).

Embodiment 4: The polypeptide of any one of Embodiments 1-3, wherein the polypeptide comprises a linker between the VH domain and the VL domain.

Embodiment 5: The polypeptide of any one of Embodiments 1-4, wherein the polypeptide is selected from the group consisting of comprise the group consisting of Fv, Fab, Fab', F(ab)2, F(ab')2, single-chain antibody, single-chain antibody (scFV), sc(Fv)2, monovalent antibody lacking hinge region, whole antibody, disulfide-stabilized Fv (dsFv), and diabody.

Embodiment 6: The polypeptide of any one of Embodiments 1-5, wherein the polypeptide is a single-chain antibody.

Embodiment 7: The polypeptide of any one of Embodiments 1-6, wherein the polypeptide is an antibody selected from the group consisting of IgA isotype, IgD isotype, IgG isotype, IgE isotype and IgM isotype.

Embodiment 8: The polypeptide of any one of Embodiments 1-7, wherein the polypeptide is an antibody selected from the group consisting of IgG1 isotype, IgG2 isotype, IgG3 isotype and IgG4 isotype.

Embodiment 9: The polypeptide of any one of Embodiments 1-8, wherein the polypeptide further comprises a Fc region of an immunoglobulin.

Embodiment 10: The polypeptide of Embodiment 9, wherein the Fc region of an immunoglobulin is a human IgG Fc region.

Embodiment 11: The polypeptide of any one of Embodiments 1-10, wherein the VL domain comprises an amino acid sequence having at least 85% identity to the amino acid sequence:

(SEQ ID NO: 78)
DVLMTQTPLSLPVSLGDQASFSCRSSQSIVHSNGNTYLEWYLQKPGQSP

KLLIYKVSNRFSGVPDRFSGSGSGTDFTLKISRVEAEDLGVYYCFQASH

VPYTFGGGTKLELKRA.

Embodiment 12: The polypeptide of any one of Embodiments 1-11, wherein the VH domain comprises an amino acid sequence having at least 85% identity to the amino acid sequence:

(SEQ ID NO: 79)
EVQLQQSGGELVKPGASVKISCKASGYSFTGYNMNWVKQTHGKSLEWIG

NINPYYGSTRYNQKFKGKATLTVDKSSSTAYMQLNSLTYEDSAVYYCAR

DDDYGEIDYFDYWGQGTTITVYS.

Embodiment 13: The polypeptide of any one of Embodiments 1-12, wherein the polypeptide comprises an amino acid sequence having at least 85% identity to the amino acid sequence:

(SEQ ID NO: 80)
DVLMTQTPLSLPVSLGDQASFSCRSSQSIVHSNGNTYLEWYLQKPGQSP

KLLIYKVSNRFSGVPDRFSGSGSGTDFTLKISRVEAEDLGVYYCFQASH

VPYTFGGGTKLELKRAEGKSSGSGSESKASEVQLQQSGGELVKPGASVK

ISCKASGYSFTGYNMNWVKQTHGKSLEWIGNINPYYGSTRYNQKFKGKA

TLTVDKSSSTAYMQLNSLTYEDSAVYYCARDDDYGEIDYFDYWGQGTTI

TVYS.

Embodiment 14: The polypeptide of any one of Embodiments 1-13, wherein the polypeptide comprises a detectable label.

Embodiment 15: The polypeptide of any one of Embodiments 1-14, wherein the polypeptide comprises a therapeutic agent.

Embodiment 16: A composition comprising a polypeptide of any one of Embodiments 1-15.

Embodiment 17: The composition of Embodiment 16, wherein the composition comprises a pharmaceutically acceptable excipient or carrier.

Embodiment 18: The composition of any one of Embodiments 16-18, wherein the composition is formulated for self-administration.

Embodiment 19: A cell comprising a polypeptide of any one of Embodiments 1-15.

Embodiment 20: A kit comprising a polypeptide of any one of Embodiments 1-15.

Embodiment 21: An analyte detection system comprising polypeptide of any one of Embodiments 1-15.

Embodiment 22: The analyte detection system of Embodiment 21, wherein said detection system comprises spectroscopic, photochemical, biochemical, immunochemical, electrical, optical chemical detection or any combinations thereof.

Embodiment 23: The analyte detection system of any one of Embodiments 21-22, wherein said detection system comprises an enzyme-linked immunosorbent assay (ELISA), fluorescent linked immunosorbent assay (FLISA), immunofluorescent microscopy, fluorescence in situ hybridization (FISH), magnetic and/or electrochemical detection, or any other radiological, chemical, enzymatic or optical detection assay.

Embodiment 24: The analyte detection system of any one of Embodiments 21-23, wherein said detection system comprises a lateral flow assay (LFA).

Embodiment 25: Use of a polypeptide of any one of Embodiments 1-15 for detecting histamine and/or histidine.

Embodiment 26: Use of a polypeptide of any one of Embodiments 1-15 in a method of treatment.

Embodiment 27: A polynucleotide comprising a nucleotide sequence encoding a polypeptide of any one of Embodiments 1-15.

Embodiment 28: The polynucleotide of Embodiment 27, wherein the polynucleotide is comprised in a vector.

Embodiment 29: A composition comprising a polynucleotide of any one of Embodiments 27-28.

Embodiment 30: A cell comprising a polynucleotide of any one of any one of Embodiments 27-28.

Embodiment 31: A kit comprising a polynucleotide of any one of any one of Embodiments 27-28.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean$\pm$1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

As used herein, the term "polypeptide" is used herein to designate a series of amino acid residues, connected to each other by peptide bonds between the alpha-amino and carboxy groups of adjacent residues. The term "polypeptide" refers to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The term "polypeptide" is used interchangeably herein when referring to a gene product and fragments thereof. Thus, exemplary polypeptides or proteins include gene products, naturally occurring proteins, homologs, orthologs, paralogs, fragments and other equivalents, variants, portions, and analogs of the foregoing.

A polypeptide of an anti-histamine or histidine antibody molecule may be linear or branched, it may comprise modified amino acids, and it may be interrupted by non-amino acids. The antibody molecule may also be modified; for example, by disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

A "variant" of a polypeptide (for example, a variant of an antibody) comprises an amino acid sequence wherein one or more amino acid residues are inserted into, deleted from and/or substituted into the amino acid sequence relative to another polypeptide sequence. Variants (naturally occurring or otherwise), alleles, homologs, conservatively modified variants, and/or conservative substitution variants of any of the particular polypeptides described are encompassed. As to amino acid sequences, one of ordinary skill will recognize that individual substitutions, deletions or additions to a nucleic acid, peptide, polypeptide, or protein sequence which alters a single amino acid or a small percentage of amino acids in the encoded sequence is a "conservatively modified variant," where the alteration results in the substitution of an amino acid with a chemically similar amino acid and retains the desired activity of the polypeptide. Such conservatively modified variants are in addition to, and do not exclude, polymorphic variants, interspecies homologs, and alleles consistent with the disclosure. A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., inhibitory T cell activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions entails exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

The term "amino acid insertion" refers to the insertion of one or more additional amino acids into a predetermined or native amino acid sequence. The insertion can be one, two, three, four, five, or up to twenty amino acid residues.

The term "amino acid deletion" refers to removal of at least one amino acid from a predetermined or native amino acid sequence. The deletion can be one, two, three, four, five, or up to twenty amino acid residues.

In some embodiments of the various aspects described herein, the polypeptide described herein can be a variant of a sequence described herein. In some embodiments of the various aspects described herein, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan to generate and test artificial variants.

In some embodiments, a polypeptide described herein (or a nucleic acid encoding such a polypeptide) can be a functional fragment or functional portion of a larger polypeptide or an amino acid sequence as described herein. As used herein, a "functional fragment" or "functional portion" is a fragment or segment of a peptide which retains at least 50% of the wildtype reference polypeptide's activity according to the assays described below herein. A functional fragment can comprise conservative substitutions of the polypeptide or amino acid sequences disclosed herein.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The term "isolated" refers to a protein (e.g., an antibody) that is substantially free of other cellular material. In one embodiment, an isolated antibody is substantially free of other proteins from the same species. In one embodiment, an isolated antibody is expressed by a cell from a different species and is substantially free of other proteins from the different species. A protein may be rendered substantially free of naturally associated components (or components associated with the cellular expression system used to produce the antibody) by isolation, using protein purification techniques well known in the art. In one embodiment, the antibodies, or antigen binding fragments, of the invention are isolated.

The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

The term "nucleic acid" refers to a deoxyribonucleotide or ribonucleotide and polymers thereof in either single strand or double strand form. The term "nucleic acid" is used interchangeably with gene, nucleotide, polynucleotide, cDNA, DNA, and mRNA. The polynucleotides can be in the form of RNA or DNA. Polynucleotides in the form of DNA, cDNA, genomic DNA, nucleic acid analogs, and synthetic DNA are within the scope of the present invention. Unless specifically limited the term encompasses nucleic acids containing known analogues of natural nucleotides that have similar binding propertied as the natural nucleic acid. Unless specifically limited, a particular nucleotide sequence also encompasses conservatively modified variants thereof (for example, those containing degenerate codon substitutions) and complementary sequences as well as the as well as the sequences specifically described.

The polynucleotides can be composed of any polyribonucleotide or polydeoxyribonucleotide, which can be unmodified RNA or DNA or modified RNA or DNA. For example, polynucleotides can be composed of single or double stranded regions, mixed single or double stranded regions. In addition, the polynucleotides can be triple stranded regions containing RNA or DNA or both RNA and DNA. Modified polynucleotides include modified bases, such as tritylated bases or unusual bases such as inosine. A variety of modification can be made to RNA and DNA, thus polynucleotide includes chemically, enzymatically, or metabolically modified forms.

The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence, which sequence, as a result of the redundancy or degeneracy of the genetic code, encodes the same polypeptides as the DNA provided herein.

A variant DNA or amino acid sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

In some embodiments of the various aspects described herein, the degree of complementarity, when optimally aligned using a suitable alignment algorithm, is about or more than about 50%, 60%, 75%, 80%, 85%, 90%, 95%, 97.5%, 99%), or more. Optimal alignment can be determined with the use of any suitable algorithm for aligning sequences. Exemplary algorithms for determining optimal alignment include, but are not limited to, the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net).

In some embodiments of the various aspects described herein, a polypeptide, nucleic acid, or cell as described herein can be engineered. As used herein, "engineered" refers to the aspect of having been manipulated by the hand of man. For example, a polynucleotide is considered to be "engineered" when at least one aspect of the polynucleotide, e.g., its sequence, has been manipulated by the hand of man to differ from the aspect as it exists in nature.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments of the various aspects described herein, specific binding can refer to an affinity of the first entity for the second target entity which is at least 10 times, at least 50 times, at least 100 times, at least 500 times, at least 1000 times or greater than the affinity for the third non-target entity. A reagent specific for a given target is one that exhibits specific binding for that target under the conditions of the assay being utilized.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In some embodiments of any of the aspects described herein, the disclosure described herein does not concern a process for cloning animals, processes for modifying the germ line genetic identity of animals, uses of embryos for industrial or commercial purposes or processes for modifying the genetic identity of animals which are likely to cause them suffering without any substantial medical benefit to man or animal, and also animals resulting from such processes. In some embodiments of any of the aspects described herein, the technology described herein relates to cells. In some embodiments of any of the aspects described herein, the technology described herein relates to isolated cells.

Other terms are defined herein within the description of the various aspects of the invention.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The method of the invention can be used in combination with the methods and compositions for detecting small molecules in a test sample as set forth in PCT/US2019/061687 filed Nov. 15, 2019, the contents of which are incorporated herein by reference in its entirety.

The technology described herein is further illustrated by the following examples which in no way should be construed as being further limiting.

EXAMPLES

Example 1: Reverse Engineered Histamine SCFV Using Phage Display Method

Small molecule detection is a challenging field because it is difficult for an antibody to recognize and bind to a small number of functional groups. These antibodies are typically raised by conjugating the small molecule target to a larger protein carrier followed by inoculation of the animal. Such an approach has been found to be successful for a number of targets that contain multiple functional groups (for example cortisol, testosterone). However, very small molecules, such as histamine (111.14 g/mol), which consists of an imidazole ring and a short carbon chain terminated with a primary amine (FIG. 1A), still pose a challenge due in part to their limited functionalities. This is an important challenge because antibody-based diagnostics that can detect histamine with great specificity and sensitivity have great potential value for medical diagnostics (e.g., for allergy and anaphylaxis), early detection of diseases, and food safety applications.

Antibodies against histamine are typically raised by conjugating histamine to a large immunogenic protein carrier, such as bovine serum albumin (BSA) or ovalbumin (OVA) via its primary amine group. Consequently, only the imidazole will be exposed to lymphocytes, which commonly results in generation of antibodies that recognize protein-bound histamine; however, they have only limited affinity and sensitivity for free histamine (FIG. 1B). These antibodies typically perform poorly in the development of immunoassays.

Thus, there is a need to design ways to overcome this lack of specificity of currently available anti-histamine antibodies to identify those binding events that result from specific binding of free histamine molecules. Here, the inventors describe development of a novel histamine competitor molecule that can be used to develop more sensitive immunoassays and surpass the limitations of currently available low affinity anti-histamine antibodies. Furthermore, there is a requirement for a superior and more refined way to not only screen antibodies against histamine, but also raise them using the right target molecule. Finally, a similar molecular design approach could be used for both the generation of more specific antibodies directed against other small molecules, and for creating more specific binding assays using available antibodies.

Available anti-histamine antibodies bind better to histamine conjugated to a larger molecule than they do to free histamine. To overcome this issue, the inventors undertook a study to improve binding of an anti-histamine antibody, which is also referred to as wild-type or wt antibody herein. The amino acid sequence for the wild-type antibody as follows:

Heavy Chain:

(SEQ ID NO: 81)

```
EVQLQQSGGELVKPGASVKISCKASGYSFTGYNMNWVKQTHGKSLEWIG
NINPYYGSTRYNQKFKGKATLTVDKSSSTAYMQLNSLTYEDSAVYYCAR
DDDYGEIDYFDYWGQGTTITVYSAKTTPPSVYPLAPGCGDTTGSSVTLG
CLVKGYFPESVTVTWNSGSLPSGVHTFPALLQSGLYTMSSSVTVPSSTW
PSQTVTCSVAHPASSTTVDKKLEPRGPKIDPCPPCKECHKCPAPNLEGG
PSVFIFPPNIKDVLMISLSPMVTCVVVDVSEDDPDVQISWFVNNVEVHT
AQTQTHREDYNSTLRVVSALPIQHQDWMSGKEFKCKVNNKDLPAPIERT
ISKIKGLVRAPQVYILPPPAEQLSRKDVSLTCLAVGFSPEDISVEWTSN
GHTEENYKDTAPVLDSDGSYFIYSKLDIKTSKWEKTDSFSCNVRHEGLH
SFYLKKTISRSPG
```

Light Chain:

(SEQ ID NO: 84)

```
DVLMTQTPLSLPVSLGDQASFSCRSSQSIVYSSGNTYLEWYLQKPGQSP
KLLIYKVSNRFSGVPDRFSGSGSGTDFTLKISRVEAEDLGVYYCFQASH
VPYTFGGGTKLELKRADAAPTVSIFPPSSEQLTSGGASVVCFLNNFYPK
```

-continued

```
DINVKWKIDGSERQNGVLNSWTDQDSKDSTYSMSSTLTLTKDEYERHNS
YTCEATHKTSTSPIVKSFNRNEC
```

In the wild-type antibody, the CDRs for the VL domain are:

CDR1: (SEQ ID NO: 20)
QSIVYSSGNTYLE

CDR2: (SEQ ID NO: 22)
LLIYKVSNRFS

CDR3: (SEQ ID NO: 25)
FQASHVPY

In the wild-type antibody, the CDRs for the VH domain are:

CDR1: (SEQ ID NO: 2)
YSFTGYNMN

CDR2: (SEQ ID NO: 4)
WIGNINPYYGSTRY

CDR3: (SEQ ID NO: 5)
RDDDYGEIDYFDY

The inventors generated a single chain variable fragment (ScFv) using the the above noted CDRs. The VH and VL domains were linked by a peptide linker comprising the amino acid sequence EGKSSGSGSESKAS (SEQ ID NO: 26) and the ScFV had the amino acid sequence:

(SEQ ID NO: 82)

```
DVLMTQTPLSLPVSLGDQASFSCRSSQSIVYSSGNTYLEWYLQKPGQSP
KLLIYKVSNRFSGVPDRFSGSGSGTDFTLKISRVEAEDLGVYYCFQASH
VPYTFGGGTKLELKRAEGKSSGSGSESKASEVQLQQSGGELVKPGASVK
ISCKASGYSFTGYNMNWVKQTHGKSLEWIGNINPYYGSTRYNQKFKGKA
TLTVDKSSSTAYMQLNSLTYEDSAVYYCARDDDYGEIDYFDYWGQGTTI
TVYS
```

This ScFv sequence was cloned into phagemid vectors to produce phage with the ScFv fused to some of the p3 coat proteins. To identify CDRs that contact the conjugated histamine, the inventors generated individual clones with one of the six CDRs significantly mutated and tested these phages in a binding assay (Table 1). Based on this, inventors prepared a number of additional antibodies (Table 2).

TABLE 1

Clone name and CDR sequences of the identified antibodies.

| Clone Name | CDR-L1 | CDR-L2 | CDR-L3 | CDR-H1 | CDR-H2 | CDR-H3 | Binding assay |
|---|---|---|---|---|---|---|---|
| Original | QSIVYSSGNYLET (SEQ ID NO: 20) | LLIYKVSNRFS (SEQ ID NO: 22) | FQASHVPY (SEQ ID NO: 25) | YSFTGYNMN (SEQ ID NO: 2) | WIGNINPYYGSTRY (SEQ ID NO: 4) | RDDDYGEIDYFDY (SEQ ID NO: 5) | + |
| CDR-L1 mut | GVAGANAGAGALA (SEQ ID NO: 19) | LLIYKVSNRFS (SEQ ID NO: 22) | FQASHVPY (SEQ ID NO: 25) | YSFTGYNMN (SEQ ID NO: 2) | WIGNINPYYGSTRY (SEQ ID NO: 4) | RDDDYGEIDYFDY (SEQ ID NO: 5) | – |

TABLE 1-continued

Clone name and CDR sequences of the identified antibodies.

| Clone Name | CDR-L1 | CDR-L2 | CDR-L3 | CDR-H1 | CDR-H2 | CDR-H3 | Binding assay |
|---|---|---|---|---|---|---|---|
| CDR-L2 mut | QSIVYSSGNTYLE (SEQ ID NO: 20) | LLIYAVKATGA (SEQ ID NO: 21) | FQASHVPY (SEQ ID NO: 25) | YSFTGYNMN (SEQ ID NO: 2) | WIGNINPYYGSTRY (SEQ ID NO: 4) | RDDDYGEIDYFDY (SEQ ID NO: 5) | – |
| CDR-L3 mut | QSIVYSSGNTYLE (SEQ ID NO: 20) | LLIYKVSNRFS (SEQ ID NO: 22) | AGAVAVAA (SEQ ID NO: 24) | YSFTGYNMN (SEQ ID NO: 2) | WIGNINPYYGSTRY (SEQ ID NO: 4) | RDDDYGEIDYFDY (SEQ ID NO: 5) | – |
| CDR-H1 mut | QSIVYSSGNTYLE (SEQ ID NO: 20) | LLIYKVSNRFS (SEQ ID NO: 22) | FQASHVPY (SEQ ID NO: 25) | AVALGGNMN (SEQ ID NO: 1) | WIGNINPYYGSTRY (SEQ ID NO: 4) | RDDDYGEIDYFDY (SEQ ID NO: 5) | + |
| CDR-H2 mut | QSIVYSSGNTYLE (SEQ ID NO: 20) | LLIYKVSNRFS S (SEQ ID NO: 22) | FQASHVPY (SEQ ID NO: 25) | YSFTGYNMN (SEQ ID NO: 2) | WIGNIAVAIGLTRY (SEQ ID NO: 3) | RDDDYGEIDYFDY (SEQ ID NO: 5) | + |
| CDR-H3 mut | QSIVYSSGNTYLE (SEQ ID NO: 20) | LLIYKVSNRF (SEQ ID NO: 22) | FQASHVPY (SEQ ID NO: 25) | YSFTGYNMN (SEQ ID NO: 2) | WIGNINPYYGSTRY (SEQ ID NO: 4) | RAGVKGNILAAGN (SEQ ID NO: 83) | – |

TABLE 2

Antibodies identified with improved binding characteristics:

| Antibody # | CDR-L1 Sequence | CDR-L3 sequence | Binding Assay |
|---|---|---|---|
| Wyss-aHM-1 | QSIVHSNGNTYLE (SEQ ID NO: 6) | FQASHVPY (SEQ ID NO: 25) | + |
| Wyss-aHM-2 | QSLVHSGGNTYLE (SEQ ID NO: 7) | FQASHVPY (SEQ ID NO: 25) | |
| Wyss-aHM-3 | QSIVHSSGNTYLE (SEQ ID NO: 8) | FQASHVPY (SEQ ID NO: 25) | |
| Wyss-aHM-4 | QSLVHSSGNTYLE (SEQ ID NO: 9) | FQASHVPY (SEQ ID NO: 25) | |
| Wyss-aHM-5 | QSIVHSGGNTYLE (SEQ ID NO: 10) | FQASHVPY (SEQ ID NO: 25) | |
| Wyss-aHM-6 | QTIVHSNGNTYLE (SEQ ID NO: 11) | SQATHVPY (SEQ ID NO: 23) | |
| Wyss-aHM-7 | QSIVHSDGNTYLE (SEQ ID NO: 12) | FQASHVPY (SEQ ID NO: 25) | |
| Wyss-aHM-8 | QSIVSSSGNTYLE (SEQ ID NO: 13) | FQASHVPY (SEQ ID NO: 25) | |
| Wyss-aHM-9 | QSIVYSDGNTYLE (SEQ ID NO: 14) | FQASHVPY (SEQ ID NO: 25) | |
| Wyss-aHM-10 | QTIVHSSGNTYLE (SEQ ID NO: 15) | FQASHVPY (SEQ ID NO: 25) | |
| Wyss-aHM-11 | QSIVHRDGNTYLE (SEQ ID NO: 16) | FQASHVPY (SEQ ID NO: 25) | |
| Wyss-aHM-12 | QSLVHSDGNTYLE (SEQ ID NO: 17) | FQASHVPY (SEQ ID NO: 25) | |
| Wyss-aHM-13 | QTIVHSNGNTYLE (SEQ ID NO: 18) | FQASHVPY (SEQ ID NO: 25) | |
| Wild type | QSIVYSSGNTYLE (SEQ ID NO: 20) | FQASHVPY (SEQ ID NO: 25) | |

Figure 2A:
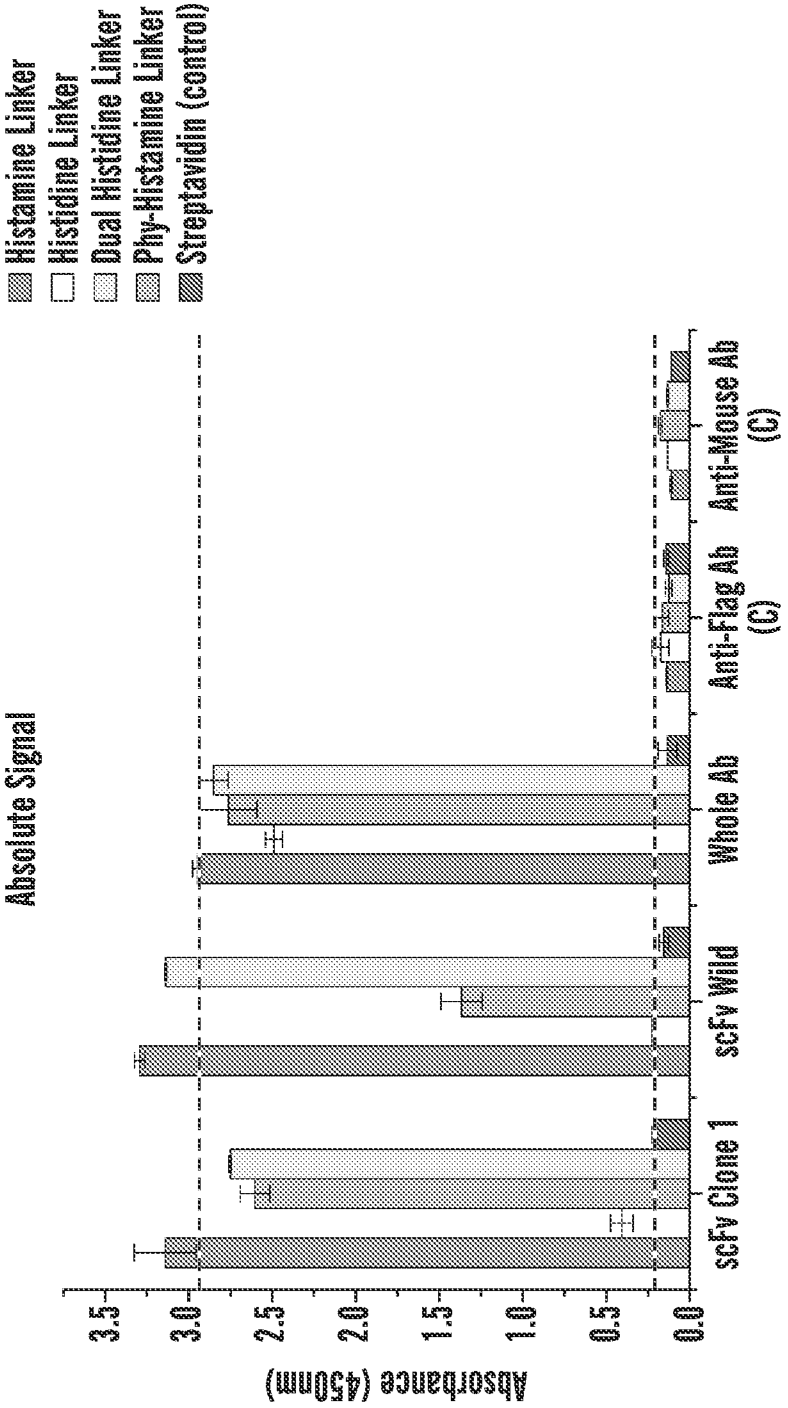
FIG. 2A shows the result of an ELISA plate assay to evaluate the binding of scFv Clone 1 with scFV wild type and full wild antibody using different linkers. The graph depicted shows the absolute absorbance values.
Figure 2B:
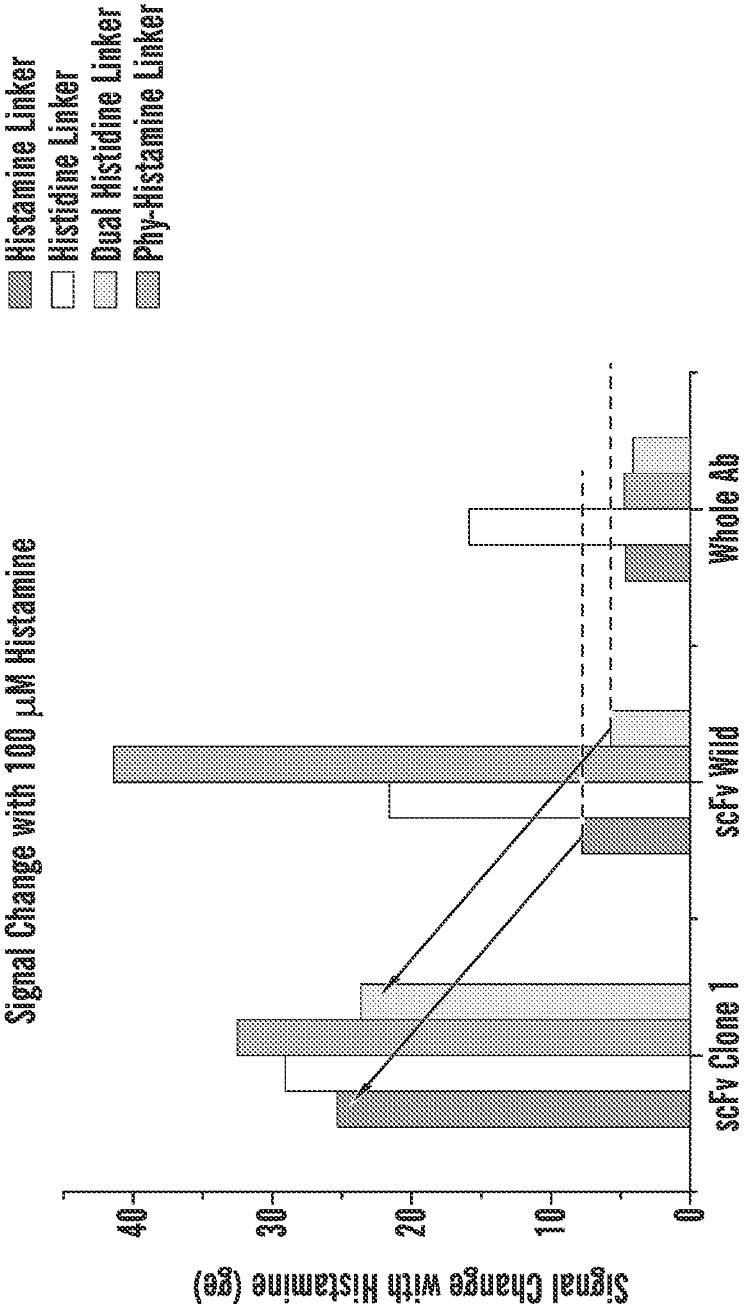
FIG. 2B shows a graph depicting the signal change with free histamine.
Figure 2C:
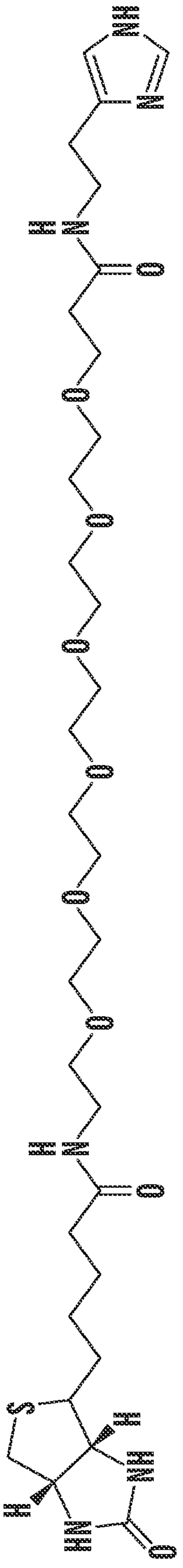
FIGS. 2C-2F show structures of a Biotin-PEG-histamine molecule (FIG. 2C). a Biotin-PEG-mono-histidine (FIG. 2D), a Biotin-PEG-dual histidine molecule (FIG. 2E) and a (FIG. 2F).
Figure 2D:
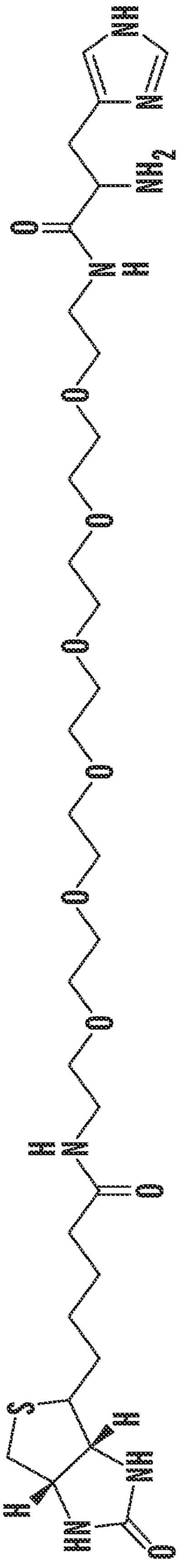
Figure 2E:
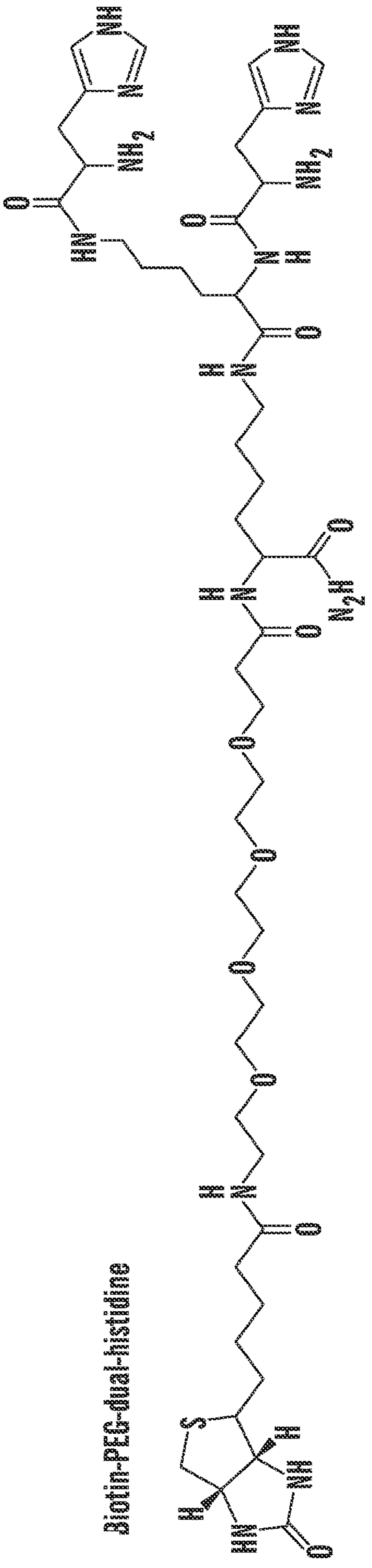
Figure 2F:
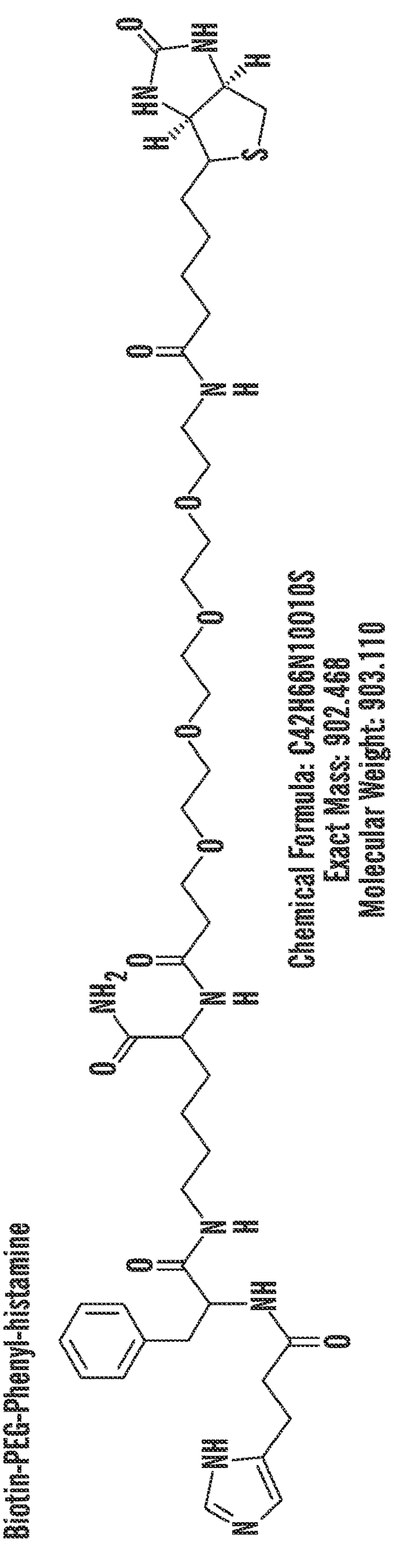

FIG. 2A and FIG. 2B present the results of the ELISA binding assay with Wyss-aHM-1 compared to scFv wildtype and full antibody wild type. Briefly, High binding ELISA plates were first functionalized with streptavidin by passive absorption and the resulting plates blocked with BSA to reduce non-specific binding and background signal. Thereafter, 25 μM linkers (biotin-PEG histamine, biotin-PEG mono histidine, biotin-PEG Phenyl histamine, biotin-PEG dual histidine) were incubated for 1 hour at room temperature on a shaker. The developed plate was then used to perform the binding assay. The wells were then tested for binding with scFv Flag-tagged (0.1 ug/mL) with or without free histamine for two hours. The incubation time was kept long so that full equilibrium is reached in the wells. As a result, the probes (scFV, Ab) are given enough time to bind and replace all weak binding with strong binding. Finally, anti-Flag tag IgG labelled horse radish peroxidase (HRP) was used to detect the bound antibodies. The presence of HRP was revealed using 3,3',5,5'-Tetramethylbenzidine (TMB) substrate, followed by stop stolution and quantified colorimetrically at 450 nm.

The graph depicted in FIG. 2A shows that scFv clone 1 demonstrates nearly the same level of binding to linkers as compared to the wild type. Interestingly, both clone 1 and wildtype scFv shows significantly reduced (5 times less) binding to single histidine linker compared to full antibody. This could be attributed to lower affinity towards free histamine. However, when these probes were challenged with free histamine in the solution, a significant increase in binding was observed with scFV clone-1 compared to wild type scFV and full antibody. Nearly 5 times improvement in binding was observed with biotin-PEG histamine and biotin-PEG Phenyl histamine demonstrating higher affinity towards free histamine compared to conjugates.

Sequence for Wyss-aHM-1, with CDRs underlined, is shown below:

(SEQ ID NO: 80)

```
DVLMTQTPLSLPVSLGDQASFSCRSSQSIVHSNGNTYLEWYLQKPGQSP
KLLIYKVSNRFSGVPDRFSGSGSGTDFTLKISRVEAEDLGVYYCFQASH
VPYTFGGGTKLELKRAEGKSSGSGSESKASEVQLQQSGGELVKPGASVK
ISCKASGYSFTGYNMNWVKQTHGKSLEWIGNINPYYGSTRYNQKFKGKA
TLTVDKSSSTAYMQLNSLTYEDSAVYYCARDDDYGEIDYFDYWGQGTTI
TVYS
```

REFERENCES

1. Dale H D, Laidlaw P D. The physiological action of β-iminazolyl-ethylamine. J Physiol (Lond) 1910; 41:318-44.
2. Steinhoff M, Griffiths C, Church M, Lugar T A. Histamine. In: Burns T, Breathnach S, Cox N, Griffiths C. eds. Rook's textbook of dermatology. Oxford, United Kingdom: Blackwell Science, 2004:9.50-2.
3. Maintz L, Novak N, Histamine and histamine intolerance. The American Journal of Clinical Nutrition, Volume 85, Issue 5, May 2007, Pages 1185-1196.

Sequences

1. VH CDR1:
   a. AVALGGNMN (SEQ ID NO: 1), and
   b. YSFTGYNMN (SEQ ID NO: 2);
2. VH CDR2:
   a. WIGNIAVAIGLTRY (SEQ ID NO: 3), and
   b. WIGNINPYYGSTRY (SEQ ID NO: 4);
3. VH CDR3:
   a. RDDDYGEIDYFDY (SEQ ID NO: 5), and
   b. RAGVKGNILAAGN (SEQ ID NO: 83);
4. VL CDR1:
   a. QSIVHSNGNTYLE (SEQ ID NO: 6),
   b. QSLVHSGGNTYLE (SEQ ID NO: 7),
   c. QSIVHSSGNTYLE (SEQ ID NO: 8),
   d. QSLVHSSGNTYLE (SEQ ID NO: 9),
   e. QSIVHSGGNTYLE (SEQ ID NO: 10),
   f. QTIVHSNGNTYLE (SEQ ID NO: 11),
   g. QSIVHSDGNTYLE (SEQ ID NO: 12),
   h. QSIVSSSGNTYLE (SEQ ID NO: 13),
   i. QSIVYSDGNTYLE (SEQ ID NO: 14),
   j. QTIVHSSGNTYLE (SEQ ID NO: 15),
   k. QSIVHRDGNTYLE (SEQ ID NO: 16),
   l. QSLVHSDGNTYLE (SEQ ID NO: 17),
   m. QTIVHSNGNTYLE (SEQ ID NO: 18),
   n. GVAGANAGAGALA (SEQ ID NO: 19), and
   o. QSIVYSSGNTYLE (SEQ ID NO: 20);
5. VL CDR2:
   a. LLIYAVKATGA (SEQ ID NO: 21), and
   b. LLIYKVSNRFS (SEQ ID NO: 22);
6. VL CDR3:
   a. SQATHVPY (SEQ ID NO: 23),
   b. AGAVAVAA (SEQ ID NO: 24), and
   c. FQASHVPY (SEQ ID NO: 25);
7. Linker:
   a. EGKSSGSGSESKAS (SEQ ID NO: 26),
   b. $(Gly_xSer)_n$, where x is 2, 3, 4, 5 or 6, and n is 1, 2, 3, 4, 5, 6, 7, 8, 9 or 10 (SEQ ID NOs: 27-76), and
   c. HHHHHH (SEQ ID NO: 77);
8. VL domain:

(SEQ ID NO: 78)

```
DVLMTQTPLSLPVSLGDQASFSCRSSQSIVHSNGNTYLEWYLQKPGQSP
KLLIYKVSNRFSGVPDRFSGSGSGTDFTLKISRVEAEDLGVYYCFQASH
VPYTFGGGTKLELKRA.
```

9. VH domain:

(SEQ ID NO: 79)

```
EVQLQQSGGELVKPGASVKISCKASGYSFTGYNMNWVKQTHGKSLEWIG
NINPYYGSTRYNQKFKGKATLTVDKSSSTAYMQLNSLTYEDSAVYYCAR
DDDYGEIDYFDYWGQGTTITVYS;
```

10. Wyss-aHM-1:

(SEQ ID NO: 80)

```
DVLMTQTPLSLPVSLGDQASFSCRSSQSIVHSNGNTYLEWYLQKPGQSP
KLLIYKVSNRFSGVPDRFSGSGSGTDFTLKISRVEAEDLGVYYCFQASH
VPYTFGGGTKLELKRAEGKSSGSGSESKASEVQLQQSGGELVKPGASVK
ISCKASGYSFTGYNMNWVKQTHGKSLEWIGNINPYYGSTRYNQKFKGKA
TLTVDKSSSTAYMQLNSLTYEDSAVYYCARDDDYGEIDYFDYWGQGTTI
TVYS.
```

11. Wild-type Heavy Chain:

(SEQ ID NO: 81)

```
EVQLQQSGGELVKPGASVKISCKASGYSFTGYNMNWVKQTHGKSLEWIG
NINPYYGSTRYNQKFKGKATLTVDKSSSTAYMQLNSLTYEDSAVYYCAR
DDDYGEIDYFDYWGQGTTITVYSAKTTPPSVYPLAPGCGDTTGSSVTLG
CLVKGYFPESVTVTWNSGSLPSGVHTFPALLQSGLYTMSSSVTVPSSTW
PSQTVTCSVAHPASSTTVDKKLEPRGPKIDPCPPCKECHKCPAPNLEGG
PSVFIFPPNIKDVLMISLSPMVTCVVVDVSEDDPDVQISWFVNNVEVHT
AQTQTHREDYNSTLRVVSALPIQHQDWMSGKEFKCKVNNKDLPAPIERT
```

-continued

ISKIKGLVRAPQVYILPPPAEQLSRKDVSLTCLAVGFSPEDISVEWTSN

GHTEENYKDTAPVLDSDGSYFIYSKLDIKTSKWEKTDSFSCNVRHEGLH

SFYLKKTISRSPG;

12. Wild-type Light Chain:

(SEQ ID NO: 84)
DVLMTQTPLSLPVSLGDQASFSCRSSQSIVYSSGNTYLEWYLQKPGQSP

KLLIYKVSNRFSGVPDRFSGSGSGTDFTLKISRVEAEDLGVYYCFQASH

VPYTFGGGTKLELKRADAAPTVSIFPPSSEQLTSGGASVVCFLNNFYPK

-continued

DINVKWKIDGSERQNGVLNSWTDQDSKDSTYSMSSTLTLTKDEYERHNS

YTCEATHKTSTSPIVKSFNRNEC; and

13. ScFV:

(SEQ ID NO: 82)
DVLMTQTPLSLPVSLGDQASFSCRSSQSIVYSSGNTYLEWYLQKPGQSP

KLLIYKVSNRFSGVPDRFSGSGSGTDFTLKISRVEAEDLGVYYCFQASH

VPYTFGGGTKLELKRAEGKSSGSGSESKASEVQLQQSGGELVKPGASVK

ISCKASGYSFTGYNMNWVKQTHGKSLEWIGNINPYYGSTRYNQKFKGKA

TLTVDKSSSTAYMQLNSLTYEDSAVYYCARDDDYGEIDYFDYWGQGTTI

TVYS.

What is claimed is:

1. A histamine binding polypeptide comprising:

a. a variable heavy chain (VH) domain comprising:

i. a complementarity determining region 1 (VH CDR1) comprising the amino acid sequence YSFTGYNMN (SEQ ID NO: 2), ii. a complementarity determining region 2 (VH CDR2) comprising the amino acid sequence WIGNINPYYGSTRY (SEQ ID NO: 4), and iii. a complementarity determining region 3 (VH CDR3) comprising the amino acid sequence RDDDYGEIDYFDY (SEQ ID NO: 5), and b. a variable light chain (VL) domain comprising:

i. a complementarity determining region 1 (VL CDR1) comprising the amino acid sequence QSIVHSNGNTYLE (SEQ ID NO: 6), ii. a complementarity determining region 2 (VL CDR2) comprising the amino acid sequence LLIYKVSNRFS (SEQ ID NO: 22); and iii. a complementarity determining region 3 (VL CDR3) comprising the amino acid sequence FQASHVPY (SEQ ID NO: 25).

2. The histamine binding polypeptide of claim 1, wherein the polypeptide comprises a linker between the VH domain and the VL domain.

3. The histamine binding polypeptide of claim 1, wherein the polypeptide is selected from the group consisting of Fv, Fab, Fab', F(ab)2, F(ab')2, single-chain antibody, single-chain antibody (scFV), sc(Fv)2, monovalent antibody lacking hinge region, whole antibody, disulfide-stabilized Fv (dsFv), and diabody.

4. The histamine binding polypeptide of claim 3, wherein the polypeptide is a single-chain antibody.

5. The histamine binding polypeptide of claim 4, wherein the polypeptide is an antibody selected from the group consisting of IgA isotype, IgD isotype, IgG isotype, IgE isotype and IgM isotype.

6. The histamine binding polypeptide of claim 5, wherein the polypeptide is an antibody selected from the group consisting of IgG1 isotype, IgG2 isotype, IgG3 isotype and IgG4 isotype.

7. The histamine binding polypeptide of claim 4, wherein the polypeptide further comprises a Fc region of an immunoglobulin.

8. The histamine binding polypeptide of claim 7, wherein the Fc region of an immunoglobulin is a human IgG Fc region.

9. The histamine binding polypeptide of claim 1, wherein the VL domain comprises the amino acid sequence:

(SEQ ID NO: 78)
DVLMTQTPLSLPVSLGDQASFSCRSSQSIVHSNGNTYLEWYLQKPGQSP
KLLIYKVSNRFSGVPDRFSGSGSGTDFTLKISRVEAEDLGVYYCFQASH
VPYTFGGGTKLELKRA.

10. The histamine binding polypeptide of claim 1, wherein the VH domain comprises the amino acid sequence:

(SEQ ID NO: 79)
EVQLQQSGGELVKPGASVKISCKASGYSFTGYNMNWVKQTHGKSLEWIG
NINPYYGSTRYNQKFKGKATLTVDKSSSTAYMQLNSLTYEDSAVYYCAR
DDDYGEIDYFDYWGQGTTITVYS.

11. The histamine binding polypeptide of claim 1, wherein the polypeptide comprises the amino acid sequence:

(SEQ ID NO: 80)
DVLMTQTPLSLPVSLGDQASFSCRSSQSIVHSNGNTYLEWYLQKPGQSP
KLLIYKVSNRFSGVPDRFSGSGSGTDFTLKISRVEAEDLGVYYCFQASH
VPYTFGGGTKLELKRAEGKSSGSGSESKASEVQLQQSGGELVKPGASVK
ISCKASGYSFTGYNMNWVKQTHGKSLEWIGNINPYYGSTRYNQKFKGKA
TLTVDKSSSTAYMQLNSLTYEDSAVYYCARDDDYGEIDYFDYWGQGTTI
TVYS.

12. The histamine binding polypeptide of claim 1, wherein the polypeptide comprises a detectable label.

13. The histamine binding polypeptide of claim 1, wherein the polypeptide comprises a therapeutic agent.

14. The histamine binding polypeptide of claim 2, wherein the linker comprises the amino acid sequence EGKSSGSGSESKAS (SEQ ID NO: 26).

* * * * *

SEQUENCE LISTING

```
<160> NUMBER OF SEQ ID NOS: 84

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Val Ala Leu Gly Gly Asn Met Asn
1               5


<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Ser Phe Thr Gly Tyr Asn Met Asn
1               5


<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Ile Gly Asn Ile Ala Val Ala Ile Gly Leu Thr Arg Tyr
1               5                   10


<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

Trp Ile Gly Asn Ile Asn Pro Tyr Tyr Gly Ser Thr Arg Tyr
1 5 10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Arg Asp Asp Asp Tyr Gly Glu Ile Asp Tyr Phe Asp Tyr
1 5 10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Gln Ser Ile Val His Ser Asn Gly Asn Thr Tyr Leu Glu
1 5 10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Gln Ser Leu Val His Ser Gly Gly Asn Thr Tyr Leu Glu
1 5 10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Gln Ser Ile Val His Ser Ser Gly Asn Thr Tyr Leu Glu
1 5 10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Gln Ser Leu Val His Ser Ser Gly Asn Thr Tyr Leu Glu
1 5 10

<210> SEQ ID NO 10
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 10

Gln Ser Ile Val His Ser Gly Gly Asn Thr Tyr Leu Glu
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Thr Ile Val His Ser Asn Gly Asn Thr Tyr Leu Glu
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ser Ile Val His Ser Asp Gly Asn Thr Tyr Leu Glu
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ser Ile Val Ser Ser Ser Gly Asn Thr Tyr Leu Glu
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Ile Val Tyr Ser Asp Gly Asn Thr Tyr Leu Glu
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Thr Ile Val His Ser Ser Gly Asn Thr Tyr Leu Glu
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Gln Ser Ile Val His Arg Asp Gly Asn Thr Tyr Leu Glu
1 5 10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Gln Ser Leu Val His Ser Asp Gly Asn Thr Tyr Leu Glu
1 5 10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Gln Thr Ile Val His Ser Asn Gly Asn Thr Tyr Leu Glu
1 5 10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Gly Val Ala Gly Ala Asn Ala Gly Ala Gly Ala Leu Ala
1 5 10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Gln Ser Ile Val Tyr Ser Ser Gly Asn Thr Tyr Leu Glu
1 5 10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Leu Leu Ile Tyr Ala Val Lys Ala Thr Gly Ala
1 5 10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Leu Leu Ile Tyr Lys Val Ser Asn Arg Phe Ser
1 5 10

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Ser Gln Ala Thr His Val Pro Tyr
1 5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Ala Gly Ala Val Ala Val Ala Ala
1 5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Phe Gln Ala Ser His Val Pro Tyr
1 5

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Glu Gly Lys Ser Ser Gly Ser Gly Ser Glu Ser Lys Ala Ser
1 5 10

<210> SEQ ID NO 27
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Gly Gly Ser
1

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Gly Gly Ser Gly Gly Ser
1 5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Gly Gly Ser Gly Gly Ser Gly Gly Ser
1 5

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Gly Gly Ser Gly Gly Ser Gly Gly Ser Gly Gly Ser
1 5 10

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Gly Gly Ser Gly Gly Ser Gly Gly Ser Gly Gly Ser Gly Gly Ser
1 5 10 15

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Gly Gly Ser Gly Gly Ser Gly Gly Ser Gly Gly Ser Gly Gly Ser Gly
1 5 10 15

Gly Ser

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Gly Gly Ser Gly Gly Ser Gly Gly Ser Gly Gly Ser Gly Gly Ser Gly
1               5                   10                  15

Gly Ser Gly Gly Ser
            20
```

<210> SEQ ID NO 34
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Gly Gly Ser Gly Gly Ser Gly Gly Ser Gly Gly Ser Gly Gly Ser Gly
1               5                   10                  15

Gly Ser Gly Gly Ser Gly Gly Ser
            20
```

<210> SEQ ID NO 35
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser
            20                  25
```

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30
```

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Ser
1

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Gly Gly Gly Ser Gly Gly Gly Ser
1 5

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Gly Gly Gly Ser Gly Gly Gly Ser Gly Gly Gly Ser
1 5 10

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Gly Gly Gly Ser Gly Gly Gly Ser Gly Gly Gly Ser Gly Gly Gly Ser
1 5 10 15

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Gly Gly Gly Ser Gly Gly Gly Ser Gly Gly Gly Ser Gly Gly Gly Ser
1 5 10 15

Gly Gly Gly Ser
20

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Gly Gly Gly Ser Gly Gly Gly Ser Gly Gly Gly Ser Gly Gly Gly Ser
1 5 10 15

Gly Gly Gly Ser Gly Gly Gly Ser

20

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Gly Gly Gly Ser Gly Gly Gly Ser Gly Gly Gly Ser Gly Gly Gly Ser
1 5 10 15

Gly Gly Gly Ser Gly Gly Gly Ser Gly Gly Gly Ser
20 25

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 44

Gly Gly Gly Ser Gly Gly Gly Ser Gly Gly Gly Ser Gly Gly Gly Ser
1 5 10 15

Gly Gly Gly Ser Gly Gly Gly Ser Gly Gly Gly Ser Gly Gly Gly Ser
20 25 30

<210> SEQ ID NO 45
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 45

Gly Gly Gly Ser Gly Gly Gly Ser Gly Gly Gly Ser Gly Gly Gly Ser
1 5 10 15

Gly Gly Gly Ser Gly Gly Gly Ser Gly Gly Gly Ser Gly Gly Gly Ser
20 25 30

Gly Gly Gly Ser
35

<210> SEQ ID NO 46
<211> LENGTH: 40
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 46

Gly Gly Gly Ser Gly Gly Gly Ser Gly Gly Gly Ser Gly Gly Gly Ser
1 5 10 15

Gly Gly Gly Ser Gly Gly Gly Ser Gly Gly Gly Ser Gly Gly Gly Ser
20 25 30

Gly Gly Gly Ser Gly Gly Gly Ser
35 40

<210> SEQ ID NO 47
<211> LENGTH: 5

<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Gly Gly Gly Gly Ser
1 5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Gly Gly Gly Gly Ser Gly Gly Gly Gly Ser
1 5 10

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Gly Gly Gly Gly Ser Gly Gly Gly Gly Ser Gly Gly Gly Gly Ser
1 5 10 15

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Gly Gly Gly Gly Ser Gly Gly Gly Gly Ser Gly Gly Gly Gly Ser Gly
1 5 10 15

Gly Gly Gly Ser
20

<210> SEQ ID NO 51
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 52
<211> LENGTH: 30
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 52

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser
20 25 30

<210> SEQ ID NO 53
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser
35

<210> SEQ ID NO 54
<211> LENGTH: 40
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 54

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser
35 40

<210> SEQ ID NO 55
<211> LENGTH: 45
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 55

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser
35 40 45

<210> SEQ ID NO 56
<211> LENGTH: 50
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 56

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50
```

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

```
Gly Gly Gly Gly Gly Ser
1               5
```

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

```
Gly Gly Gly Gly Gly Ser Gly Gly Gly Gly Gly Ser
1               5                   10
```

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

```
Gly Gly Gly Gly Gly Ser Gly Gly Gly Gly Gly Ser Gly Gly Gly Gly
1               5                   10                  15

Gly Ser
```

<210> SEQ ID NO 60
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

```
Gly Gly Gly Gly Gly Ser Gly Gly Gly Gly Gly Ser Gly Gly Gly Gly
1               5                   10                  15

Gly Ser Gly Gly Gly Gly Gly Ser
            20
```

<210> SEQ ID NO 61
<211> LENGTH: 30

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 61

Gly Gly Gly Gly Gly Ser Gly Gly Gly Gly Gly Ser Gly Gly Gly Gly
1 5 10 15

Gly Ser Gly Gly Gly Gly Gly Ser Gly Gly Gly Gly Gly Ser
20 25 30

<210> SEQ ID NO 62
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 62

Gly Gly Gly Gly Gly Ser Gly Gly Gly Gly Gly Ser Gly Gly Gly Gly
1 5 10 15

Gly Ser Gly Gly Gly Gly Gly Ser Gly Gly Gly Gly Gly Ser Gly Gly
20 25 30

Gly Gly Gly Ser
35

<210> SEQ ID NO 63
<211> LENGTH: 42
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 63

Gly Gly Gly Gly Gly Ser Gly Gly Gly Gly Gly Ser Gly Gly Gly Gly
1 5 10 15

Gly Ser Gly Gly Gly Gly Gly Ser Gly Gly Gly Gly Gly Ser Gly Gly
20 25 30

Gly Gly Gly Ser Gly Gly Gly Gly Gly Ser
35 40

<210> SEQ ID NO 64
<211> LENGTH: 48
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 64

Gly Gly Gly Gly Gly Ser Gly Gly Gly Gly Gly Ser Gly Gly Gly Gly
1 5 10 15

Gly Ser Gly Gly Gly Gly Gly Ser Gly Gly Gly Gly Gly Ser Gly Gly
20 25 30

Gly Gly Gly Ser Gly Gly Gly Gly Gly Ser Gly Gly Gly Gly Gly Ser
35 40 45

<210> SEQ ID NO 65
<211> LENGTH: 54
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 65

Gly Gly Gly Gly Gly Ser Gly Gly Gly Gly Gly Ser Gly Gly Gly Gly
1 5 10 15

Gly Ser Gly Gly Gly Gly Gly Ser Gly Gly Gly Gly Gly Ser Gly Gly
20 25 30

Gly Gly Gly Ser Gly Gly Gly Gly Gly Ser Gly Gly Gly Gly Gly Ser
35 40 45

Gly Gly Gly Gly Gly Ser
50

<210> SEQ ID NO 66
<211> LENGTH: 60
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 66

Gly Gly Gly Gly Gly Ser Gly Gly Gly Gly Gly Ser Gly Gly Gly Gly
1 5 10 15

Gly Ser Gly Gly Gly Gly Gly Ser Gly Gly Gly Gly Gly Ser Gly Gly
20 25 30

Gly Gly Gly Ser Gly Gly Gly Gly Gly Ser Gly Gly Gly Gly Gly Ser
35 40 45

Gly Gly Gly Gly Gly Ser Gly Gly Gly Gly Gly Ser
50 55 60

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Gly Gly Gly Gly Gly Gly Ser
1 5

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Gly Gly Gly Gly Gly Gly Ser Gly Gly Gly Gly Gly Gly Ser
1 5 10

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Gly Gly Gly Gly Gly Gly Ser Gly Gly Gly Gly Gly Gly Ser Gly Gly
1 5 10 15

Gly Gly Gly Gly Ser
20

<210> SEQ ID NO 70
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Gly Gly Gly Gly Gly Gly Ser Gly Gly Gly Gly Gly Gly Ser Gly Gly
1 5 10 15

Gly Gly Gly Gly Ser Gly Gly Gly Gly Gly Gly Ser
20 25

<210> SEQ ID NO 71
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Gly Gly Gly Gly Gly Gly Ser Gly Gly Gly Gly Gly Gly Ser Gly Gly
1 5 10 15

Gly Gly Gly Gly Ser Gly Gly Gly Gly Gly Gly Ser Gly Gly Gly Gly
20 25 30

Gly Gly Ser
35

<210> SEQ ID NO 72
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

Gly Gly Gly Gly Gly Gly Ser Gly Gly Gly Gly Gly Gly Ser Gly Gly
1 5 10 15

Gly Gly Gly Gly Ser Gly Gly Gly Gly Gly Gly Ser Gly Gly Gly Gly
20 25 30

Gly Gly Ser Gly Gly Gly Gly Gly Gly Ser
35 40

<210> SEQ ID NO 73
<211> LENGTH: 49
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

Gly Gly Gly Gly Gly Gly Ser Gly Gly Gly Gly Gly Gly Ser Gly Gly
1 5 10 15

Gly Gly Gly Gly Ser Gly Gly Gly Gly Gly Gly Ser Gly Gly Gly Gly 20 25 30

Gly Gly Ser Gly Gly Gly Gly Gly Gly Ser Gly Gly Gly Gly Gly Gly
35 40 45

Ser

<210> SEQ ID NO 74
<211> LENGTH: 56
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Gly Gly Gly Gly Gly Gly Ser Gly Gly Gly Gly Gly Gly Ser Gly Gly
1 5 10 15

Gly Gly Gly Gly Ser Gly Gly Gly Gly Gly Gly Ser Gly Gly Gly Gly
20 25 30

Gly Gly Ser Gly Gly Gly Gly Gly Gly Ser Gly Gly Gly Gly Gly Gly
35 40 45

Ser Gly Gly Gly Gly Gly Gly Ser
50 55

<210> SEQ ID NO 75
<211> LENGTH: 63
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

Gly Gly Gly Gly Gly Gly Ser Gly Gly Gly Gly Gly Gly Ser Gly Gly
1 5 10 15

Gly Gly Gly Gly Ser Gly Gly Gly Gly Gly Gly Ser Gly Gly Gly Gly
20 25 30

Gly Gly Ser Gly Gly Gly Gly Gly Gly Ser Gly Gly Gly Gly Gly Gly
35 40 45

Ser Gly Gly Gly Gly Gly Gly Ser Gly Gly Gly Gly Gly Gly Ser
50 55 60

<210> SEQ ID NO 76
<211> LENGTH: 70
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

Gly Gly Gly Gly Gly Gly Ser Gly Gly Gly Gly Gly Gly Ser Gly Gly
1 5 10 15

Gly Gly Gly Gly Ser Gly Gly Gly Gly Gly Gly Ser Gly Gly Gly Gly
20 25 30

Gly Gly Ser Gly Gly Gly Gly Gly Gly Ser Gly Gly Gly Gly Gly Gly
35 40 45

Ser Gly Gly Gly Gly Gly Gly Ser Gly Gly Gly Gly Gly Gly Ser Gly
50 55 60

Gly Gly Gly Gly Gly Ser
65 70

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 77

His His His His His His
1 5

<210> SEQ ID NO 78
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 78

Asp Val Leu Met Thr Gln Thr Pro Leu Ser Leu Pro Val Ser Leu Gly
1 5 10 15

Asp Gln Ala Ser Phe Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Ala
85 90 95

Ser His Val Pro Tyr Thr Phe Gly Gly Gly Thr Lys Leu Glu Leu Lys
100 105 110

Arg Ala

<210> SEQ ID NO 79
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 79

Glu Val Gln Leu Gln Gln Ser Gly Gly Glu Leu Val Lys Pro Gly Ala
1 5 10 15

Ser Val Lys Ile Ser Cys Lys Ala Ser Gly Tyr Ser Phe Thr Gly Tyr
20 25 30

Asn Met Asn Trp Val Lys Gln Thr His Gly Lys Ser Leu Glu Trp Ile
35 40 45

Gly Asn Ile Asn Pro Tyr Tyr Gly Ser Thr Arg Tyr Asn Gln Lys Phe
50 55 60

Lys Gly Lys Ala Thr Leu Thr Val Asp Lys Ser Ser Ser Thr Ala Tyr
65 70 75 80

Met Gln Leu Asn Ser Leu Thr Tyr Glu Asp Ser Ala Val Tyr Tyr Cys
85 90 95

Ala Arg Asp Asp Asp Tyr Gly Glu Ile Asp Tyr Phe Asp Tyr Trp Gly
100 105 110

Gln Gly Thr Thr Ile Thr Val Tyr Ser
115 120

<210> SEQ ID NO 80
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

Asp Val Leu Met Thr Gln Thr Pro Leu Ser Leu Pro Val Ser Leu Gly
1 5 10 15

Asp Gln Ala Ser Phe Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Ala
85 90 95

Ser His Val Pro Tyr Thr Phe Gly Gly Gly Thr Lys Leu Glu Leu Lys
100 105 110

Arg Ala Glu Gly Lys Ser Ser Gly Ser Gly Ser Glu Ser Lys Ala Ser
115 120 125

Glu Val Gln Leu Gln Gln Ser Gly Gly Glu Leu Val Lys Pro Gly Ala
130 135 140

Ser Val Lys Ile Ser Cys Lys Ala Ser Gly Tyr Ser Phe Thr Gly Tyr
145 150 155 160

Asn Met Asn Trp Val Lys Gln Thr His Gly Lys Ser Leu Glu Trp Ile
165 170 175

Gly Asn Ile Asn Pro Tyr Tyr Gly Ser Thr Arg Tyr Asn Gln Lys Phe
180 185 190

Lys Gly Lys Ala Thr Leu Thr Val Asp Lys Ser Ser Ser Thr Ala Tyr
195 200 205

Met Gln Leu Asn Ser Leu Thr Tyr Glu Asp Ser Ala Val Tyr Tyr Cys
210 215 220

Ala Arg Asp Asp Asp Tyr Gly Glu Ile Asp Tyr Phe Asp Tyr Trp Gly
225 230 235 240

Gln Gly Thr Thr Ile Thr Val Tyr Ser
245

<210> SEQ ID NO 81
<211> LENGTH: 454
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

Glu Val Gln Leu Gln Gln Ser Gly Gly Glu Leu Val Lys Pro Gly Ala
1 5 10 15

Ser Val Lys Ile Ser Cys Lys Ala Ser Gly Tyr Ser Phe Thr Gly Tyr
20 25 30

```
Asn Met Asn Trp Val Lys Gln Thr His Gly Lys Ser Leu Glu Trp Ile
        35                  40                  45

Gly Asn Ile Asn Pro Tyr Tyr Gly Ser Thr Arg Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Tyr Glu Asp Ser Ala Val Tyr Tyr Cys
                85                  90                  95

Ala Arg Asp Asp Asp Tyr Gly Glu Ile Asp Tyr Phe Asp Tyr Trp Gly
            100                 105                 110

Gln Gly Thr Thr Ile Thr Val Tyr Ser Ala Lys Thr Thr Pro Pro Ser
        115                 120                 125

Val Tyr Pro Leu Ala Pro Gly Cys Gly Asp Thr Thr Gly Ser Ser Val
    130                 135                 140

Thr Leu Gly Cys Leu Val Lys Gly Tyr Phe Pro Glu Ser Val Thr Val
145                 150                 155                 160

Thr Trp Asn Ser Gly Ser Leu Pro Ser Gly Val His Thr Phe Pro Ala
                165                 170                 175

Leu Leu Gln Ser Gly Leu Tyr Thr Met Ser Ser Ser Val Thr Val Pro
            180                 185                 190

Ser Ser Thr Trp Pro Ser Gln Thr Val Thr Cys Ser Val Ala His Pro
        195                 200                 205

Ala Ser Ser Thr Thr Val Asp Lys Lys Leu Glu Pro Arg Gly Pro Lys
    210                 215                 220

Ile Asp Pro Cys Pro Pro Cys Lys Glu Cys His Lys Cys Pro Ala Pro
225                 230                 235                 240

Asn Leu Glu Gly Gly Pro Ser Val Phe Ile Phe Pro Pro Asn Ile Lys
                245                 250                 255

Asp Val Leu Met Ile Ser Leu Ser Pro Met Val Thr Cys Val Val Val
            260                 265                 270

Asp Val Ser Glu Asp Asp Pro Asp Val Gln Ile Ser Trp Phe Val Asn
        275                 280                 285

Asn Val Glu Val His Thr Ala Gln Thr Gln Thr His Arg Glu Asp Tyr
    290                 295                 300

Asn Ser Thr Leu Arg Val Val Ser Ala Leu Pro Ile Gln His Gln Asp
305                 310                 315                 320

Trp Met Ser Gly Lys Glu Phe Lys Cys Lys Val Asn Asn Lys Asp Leu
                325                 330                 335

Pro Ala Pro Ile Glu Arg Thr Ile Ser Lys Ile Lys Gly Leu Val Arg
            340                 345                 350

Ala Pro Gln Val Tyr Ile Leu Pro Pro Pro Ala Glu Gln Leu Ser Arg
        355                 360                 365

Lys Asp Val Ser Leu Thr Cys Leu Ala Val Gly Phe Ser Pro Glu Asp
    370                 375                 380

Ile Ser Val Glu Trp Thr Ser Asn Gly His Thr Glu Glu Asn Tyr Lys
385                 390                 395                 400

Asp Thr Ala Pro Val Leu Asp Ser Asp Gly Ser Tyr Phe Ile Tyr Ser
                405                 410                 415

Lys Leu Asp Ile Lys Thr Ser Lys Trp Glu Lys Thr Asp Ser Phe Ser
            420                 425                 430

Cys Asn Val Arg His Glu Gly Leu His Ser Phe Tyr Leu Lys Lys Thr
        435                 440                 445
```

Ile Ser Arg Ser Pro Gly
450

<210> SEQ ID NO 82
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

Asp Val Leu Met Thr Gln Thr Pro Leu Ser Leu Pro Val Ser Leu Gly
1 5 10 15

Asp Gln Ala Ser Phe Ser Cys Arg Ser Ser Gln Ser Ile Val Tyr Ser
20 25 30

Ser Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Ala
85 90 95

Ser His Val Pro Tyr Thr Phe Gly Gly Gly Thr Lys Leu Glu Leu Lys
100 105 110

Arg Ala Glu Gly Lys Ser Ser Gly Ser Gly Ser Glu Ser Lys Ala Ser
115 120 125

Glu Val Gln Leu Gln Gln Ser Gly Gly Glu Leu Val Lys Pro Gly Ala
130 135 140

Ser Val Lys Ile Ser Cys Lys Ala Ser Gly Tyr Ser Phe Thr Gly Tyr
145 150 155 160

Asn Met Asn Trp Val Lys Gln Thr His Gly Lys Ser Leu Glu Trp Ile
165 170 175

Gly Asn Ile Asn Pro Tyr Tyr Gly Ser Thr Arg Tyr Asn Gln Lys Phe
180 185 190

Lys Gly Lys Ala Thr Leu Thr Val Asp Lys Ser Ser Ser Thr Ala Tyr
195 200 205

Met Gln Leu Asn Ser Leu Thr Tyr Glu Asp Ser Ala Val Tyr Tyr Cys
210 215 220

Ala Arg Asp Asp Asp Tyr Gly Glu Ile Asp Tyr Phe Asp Tyr Trp Gly
225 230 235 240

Gln Gly Thr Thr Ile Thr Val Tyr Ser
245

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Arg Ala Gly Val Lys Gly Asn Ile Leu Ala Ala Gly Asn
1 5 10

<210> SEQ ID NO 84
<211> LENGTH: 219

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Val Leu Met Thr Gln Thr Pro Leu Ser Leu Pro Val Ser Leu Gly
1               5                   10                  15

Asp Gln Ala Ser Phe Ser Cys Arg Ser Ser Gln Ser Ile Val Tyr Ser
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ala
                85                  90                  95

Ser His Val Pro Tyr Thr Phe Gly Gly Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```